United States Patent
Won

(10) Patent No.: US 11,793,757 B2
(45) Date of Patent: *Oct. 24, 2023

(54) PHYSIOLOGICALLY ACTIVE SUBSTANCE CARRIER

(71) Applicant: LEMONEX INC., Seoul (KR)

(72) Inventor: Cheolhee Won, Seoul (KR)

(73) Assignee: LEMONEX INC., Seoul (KR)

(*) Notice: Subject to any disclaimer, the term of this patent is extended or adjusted under 35 U.S.C. 154(b) by 90 days.

This patent is subject to a terminal disclaimer.

(21) Appl. No.: 17/399,320

(22) Filed: Aug. 11, 2021

(65) Prior Publication Data

US 2021/0369614 A1    Dec. 2, 2021

Related U.S. Application Data

(63) Continuation of application No. 16/483,830, filed as application No. PCT/KR2018/001617 on Feb. 6, 2018, now Pat. No. 11,129,796.

(30) Foreign Application Priority Data

Feb. 6, 2018 (KR) .......................... 10-2018-0014842

(51) Int. Cl.
*A61K 9/16* (2006.01)
*A61K 31/203* (2006.01)
(Continued)

(52) U.S. Cl.
CPC .......... *A61K 9/1611* (2013.01); *A61K 31/203* (2013.01); *A61K 31/44* (2013.01);
(Continued)

(58) Field of Classification Search
CPC ................ A61K 38/00; A61K 31/4745; A61K 38/1758; A61K 9/143; A61K 39/395;
(Continued)

(56) References Cited

U.S. PATENT DOCUMENTS

2009/0181096 A1  7/2009 Ludwig
2010/0104650 A1  4/2010 Lee et al.
(Continued)

FOREIGN PATENT DOCUMENTS

CN    101652126 A    2/2010
CN    101687632 A    3/2010
(Continued)

OTHER PUBLICATIONS

Office action dated May 2, 2022 from US Patent Office in a parent U.S. Appl. No. 16/122,872.
(Continued)

*Primary Examiner* — Jianfeng Song
(74) *Attorney, Agent, or Firm* — The PL Law Group, PLLC

(57) ABSTRACT

A porous silica particles according to an embodiment of the present disclosure includes a plurality of pores with a diameter of 5 nm to 100 nm. The porous silica particles have particular physical properties, can deliver all various drugs by a supported amount in a sustained manner, and can be parenterally administered.

11 Claims, 15 Drawing Sheets

Specification includes a Sequence Listing.

Related U.S. Application Data

(60) Provisional application No. 62/455,148, filed on Feb. 6, 2017.

(51) Int. Cl.
    *A61K 31/44* (2006.01)
    *A61K 31/4745* (2006.01)
    *A61K 31/704* (2006.01)
    *A61K 31/711* (2006.01)
    *A61K 31/713* (2006.01)
    *A61K 38/17* (2006.01)
    *A61K 38/46* (2006.01)
    *A61K 39/395* (2006.01)

(52) U.S. Cl.
    CPC ........ *A61K 31/4745* (2013.01); *A61K 31/704* (2013.01); *A61K 31/711* (2013.01); *A61K 31/713* (2013.01); *A61K 38/1758* (2013.01); *A61K 38/465* (2013.01); *A61K 39/395* (2013.01)

(58) Field of Classification Search
    CPC .... A61K 31/711; A61K 31/44; A61K 38/465; A61K 48/0025; A61K 31/713; A61K 31/704; A61K 9/0019; A61K 31/203; A61K 9/1611; C01P 2006/12; C01P 2004/62; C01P 2004/64; C01P 2004/32; C12N 15/87; C01B 33/18
    See application file for complete search history.

(56) References Cited

U.S. PATENT DOCUMENTS

| | | | |
|---|---|---|---|
| 2010/0266491 | A1 | 10/2010 | Farokhzad et al. |
| 2011/0200595 | A1 | 8/2011 | Gerdes et al. |
| 2011/0256184 | A1 | 10/2011 | Lei et al. |
| 2012/0283379 | A1 | 11/2012 | Auger et al. |
| 2014/0014327 | A1 | 1/2014 | Badri et al. |
| 2014/0017327 | A1 | 1/2014 | Cheng et al. |
| 2017/0172923 | A1* | 6/2017 | Won .................. A61K 47/40 |
| 2018/0319822 | A1 | 11/2018 | Schoenfisch et al. |

FOREIGN PATENT DOCUMENTS

| | | | |
|---|---|---|---|
| CN | 103751857 A | 4/2014 | |
| CN | 105456198 A | 4/2016 | |
| CN | 105560186 A | 5/2016 | |
| EP | 3 173 074 A1 | 5/2017 | |
| EP | 3 659 585 A2 | 6/2020 | |
| JP | 2013-006859 A | 1/2013 | |
| JP | 2020-506972 A | 3/2020 | |
| KR | 10-2010-0117433 A | 11/2010 | |
| KR | 10-2011-0000297 A | 1/2011 | |
| KR | 10-2012-0025224 A | 3/2012 | |
| KR | 10-2014-0010285 A | 1/2014 | |
| KR | 10-2015-0014560 A | 2/2015 | |
| KR | 10-2016-0011565 A | 2/2016 | |
| KR | 10-2016-0137109 A | 11/2016 | |
| WO | WO 2005/097677 A1 | 10/2005 | |
| WO | WO 2008/105773 A2 | 9/2008 | |
| WO | WO-2009088250 A2 * | 7/2009 | ........... A61K 9/5115 |
| WO | WO 2009/113522 A1 | 9/2009 | |
| WO | WO 2012/149376 A2 | 11/2012 | |
| WO | WO-2016013751 A1 * | 1/2016 | ........... A61K 39/395 |
| WO | WO 2016/149378 A1 | 9/2016 | |
| WO | WO2017/008059 A1 | 1/2017 | |

OTHER PUBLICATIONS

Yixian Zhou et al., "Mesoporous silica nanoparticles for drug and gene delivery", Acta Pharmaceutica Sinica B, (80):165-177, 2018.

Park, Hui Seong, "Novel Intracellular Protein Delivery Carriers Based on PH-Responsive Mesoporous Nanoparticles", Graduate school of Ewha Womans University, Doctoral Thesis, 2011.

Kim, Se Mi, "RGD- and Hemagglutinin Peptide-conjugated Mesoporous Silica Nanoparticles in Doxorubin resistant MCF-7 Cells", Graduate school of Soongsil University, Master's Thesis, 2013. (English abstract is included in this reference.).

Choi, Ji Ung, "Multifunctional Silica-Iron Oxide Nanocontainers for Imaging and Drug Deliver", Graduate school of Inha University, Engineering Master's Thesis, 2013. (English abstract is included in this reference.).

Lin, Yu-Hsuan, Abstract of "Characterization on co-delivery of superoxide dismutase and glutathione peroxidase by using nanoparticles", National Taiwan University Thesis, 2014.

Mi-Hee Kim et al., "Facile Synthesis of Monodispersed Mesoporous Silica Nanoparticles with Ultralarge Pores and Their Application in Gene Delivery", ACS Nano (ACS Publications) , vol. 5 No. 5, pp. 3568-3576, 2011 (Abstract is submitted herewith).

Mahkam Mehrdad, "Synthesis and characterization of pH-sensitive silica nanoparticles for oral-insulin delivery", Current Drug Delivery, vol. 8, No. 6, pp. 607-611, 2011, Miyaneh, Iran, ISSN: 1875-5704, DOI: NLM21864258.

Margarita D. Popova et al., "Carboxylic modified spherical mesoporous silicas as drug delivery carriers", International Journal of Pharmaceutics, vol. 436, No. 1-2, pp. 778-785, 2012.

Meng H. et al., "Engineered Design of Mesoporous Silica Nanoparticles to Deliver Doxorubicin and P-Glycoprotein SiRNA to Overcome Drug Resistance in a Cancer Cell Line", ACS Nano, vol. 4, No. 8, pp. 4539-4550, 2010.

Lim JS et al., "Intracellular protein delivery by hollow mesoporous silica capsules with a large surface hole", Nanotechnology, vol. 23, Art. No. 085101, pp. 1-11, 2012.

Tarn D. et al., "Mesoporous Silica Nanoparticle Nanocarriers: Biofunctionality and Biocompatibility." vol. 46, No. 3. pp.792-801, 2013.

Igor I. et al., "Mesoporous Silica Nanoparticles for Intracellular Delivery of Membrane-Impermeable Proteins", Journal of the American Chemical Society vol. 129, pp. 8845-8849, 2007.

Yu-Shen Lin et al., Supporting Information, Chem. Mater. 2005, 17, 18, 4570-4573, attached hereto as Appendix 1, downloaded at https://pubs.acs.org/doi/suppl/10.1021/cm051014c/suppl_file/cm051014csi20050711_121110.pdf.

Marimar Bravo Cadena, "Application of Mesoporous Silica Nanoparticles for Biocide Delivery to Plants to Prevent Pre-Harvest Losses" A thesis submitted for the degree of Doctor of Philosophy, University of Oxford Mansfield College Department of Engineering, 2018.

J. Arbiol et al.,"Distributions of Noble Metal Pd and Pt in Mesoporous Silica", Applied Physics Letters, vol. 81, Issue 18, 2002, pp. 3449-3451.

Dongyuan Zhao et al., Nonionic Triblock and Star Diblock Copolymer and Oligomeric Surfactant Syntheses of Highly Ordered, Hydrothermally Stable, Mesoporous Silica Structures:, JACS (1998), 120; 6024-6036).

Vallet-Regi, M., et al. Bone-regenerative bioceramic implants with drug and protein controlled delivery capability, Prog. Solid State Chem. (2008), 36; 163-191.

Hye-Seon Shin et al."Facile Preparation of Ultra-Large Pore Mesoporous Silica Nanoparticles and Their Application tot eh Encapsulation of Large Guest Molecules", Applied Mater. Interfaces (Jan. 2014), 6; 1740-1746.

Fakhoury, Jean Raymond Garcia, "Porous silicon microparticles as an embolic agent for the treatment of hepatocellular carcinoma" The University of Texas at Austin, Dec. 31, 2011 (Abstract is submitted herewith.).

Kaasalainen, M. et al. "Size, Stability, and Porosity of Mesoporous Nanoparticles Characterized with Light Scattering" Nanoscale Research. Letters, vol. 12, No. 74, 2017.

Jadhav, S. A et al. "Porous Silica Particles: Synthesis, Physicochemical Characterization and Evaluation of Suspension Stability" Physical Chemistry: An Indian. Journal, vol. S1, No. 102, 2017.

(56) References Cited

OTHER PUBLICATIONS

Notice of allowance dated Jul. 12, 2022 from Japan Intellectual Property Office in a counterpart Japanese Patent Application No. 2021-056003 (all the cited references are listed in this IDS.).
Office action dated Jun. 7, 2022 from Japan Intellectual Property Office in a counterpart Japanese Patent Application No. 2021-075356 (all the cited references are listed in this IDS.).
Suparna Chakraborty et al., "Colloids and Surfaces A: Physicochemical and Engineering Aspects", 2014, vol. 455, pp. 111-121.
Jin-Gui Wang et al., "Hollow Carved Single-Crystal Mesoporous Silica Templated by Mesomorphous Polyelectrolyte Surfactant Complexes" Chem. Mater.,2010, vol. 22, pp. 3829-3831,Supporting Information(pp. 1-16).
Abdelhamid Sayari et al., "New Approaches to Pore Size Engineering of Mesoporous Silicate" Adv. Mater.,1998, vol. 10, No. 16, pp. 1376-1379.
T.V. Malleswara Rao et al., "Ethane dehydrogenation over pore-expanded mesoporous silica supported chromium oxide: 1. Catalysts preparation and characterization" Journal of Molecular Catalysis A: Chemical, 2009, vol. 301, pp. 152-158.
Wanyin Zhai et al., "Degradation of hollow mesoporous silica nanoparticles in human umbilical vein endothelial cells", J Biomed Mater Res Part B, May 7, 2012, 100B:1397-1403, Wiley Periodicals, Inc.
Office action dated Apr. 13, 2022 from US Patent Office in a parent U.S. Appl. No. 16/633,849.
Decision of Refusal dated Mar. 28, 2023 from Japan Intellectual Property Office in a counterpart Japanese Patent Application No. 2021-075356 (all the cited references are listed in this IDS.) (English translation is also submitted herewith.).
Youngjin Choi et al., "A Biodegradation Study of SBA-15 Microparticles in Simulated Body Fluid and in Vivo", Langmuir 2015, 31, pp. 6457-6462, DOI: 10.1021/acs.langmuir.5b01316.
Mamoru Mizutani et al., "Anomalous Pore Expansion of Highly Monodispersed Mesoporous Silica Spheres and Its Application to the Synthesis of Porous Ferromagnetic Composite" Chem. Mater., vol. 20, No. 14, 2008, pp. 4777-4782, DOI: 10.1021/cm702792e.

\* cited by examiner 0 hr     120 hrs     360 hrs

| Samples | $t_{50\%}$ |
|---|---|
| MSN(200)$_2$ | 17.9 h |
| DDV(200)$_{10}$ | 57.4 h |
| DDV(200)$_{17}$ | 53.6 h |

$tRC_{50}$ = ~2 days (~48 hr) (±15%)

$t(RC_{50})$ = ca. 24 h ± 15%

$t_{50}$ = ca. 5 h ± 15%

SEQUENCE LISTING

```
<160> NUMBER OF SEQ ID NOS: 7

<210> SEQ ID NO 1
<211> LENGTH: 21
<212> TYPE: RNA
<213> ORGANISM: Artificial Sequence
<220> FEATURE:
<223> OTHER INFORMATION: GFP siRNA sense

<400> SEQUENCE: 1
ggcuacgucc aggagcgcac c                                              21

<210> SEQ ID NO 2
<211> LENGTH: 21
<212> TYPE: RNA
<213> ORGANISM: Artificial Sequence
<220> FEATURE:
<223> OTHER INFORMATION: GFP siRNA antisense

<400> SEQUENCE: 2
ugcgcuccug gacguagccu u                                              21

<210> SEQ ID NO 3
<211> LENGTH: 1386
<212> TYPE: PRT
<213> ORGANISM: Artificial Sequence
<220> FEATURE:
<223> OTHER INFORMATION: Cas9

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

-continued

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

```
Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

| | | | | | | | | | | | | |
|---|---|---|---|---|---|---|---|---|---|---|---|---|
| Gly | Gly | Ser | Gly | Pro | Pro | Lys | Lys | Lys | Arg | Lys | Val | His His His |
| 1370 | | | | 1375 | | | | | 1380 | | | |
| His | His | His | | | | | | | | | | |
| | | 1385 | | | | | | | | | | |

<210> SEQ ID NO 4
<211> LENGTH: 130
<212> TYPE: RNA
<213> ORGANISM: Artificial Sequence
<220> FEATURE:
<223> OTHER INFORMATION: Guide RNA

<400> SEQUENCE: 4

```
gaaauuaaua cgacucacua uaggggccca guggaucuaa augaggggguu uuagagcuag    60
aaauagcaag uuaaaauaag gcuaguccgu uaucaacuug aaaaaguggc accgagucgg   120
ugcuuuuuuu                                                          130
```

<210> SEQ ID NO 5
<211> LENGTH: 6330
<212> TYPE: DNA
<213> ORGANISM: Artificial Sequence
<220> FEATURE:
<223> OTHER INFORMATION: plasmid DNA

<400> SEQUENCE: 5

```
gttaggcgtt ttgcgctgct tcgcgatgta cgggccagat atacgcgttg acattgatta     60
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta taagcagagc tcgtttag tgaaccgtca gatcgcctgg    660
agacgccatc cacgctgttt tgacctccat agaagacacc gggaccgatc cagcctccgg    720
actctagagg atcgaaccct tttgaccct cgtacagaag ctaatacgac tcactatagg    780
gaaataagag agaaaagaag agtaagaaga aatataagag ccaccatggt gagcaagggc    840
gaggagctgt tcaccggggt ggtgcccatc ctggtcgagc tggacggcga cgtaaacggc    900
cacaagttca gcgtgtccgg cgagggcgag ggcgatgcca cctacggcaa gctgaccctg    960
aagttcatct gcaccaccgg caagctgccc gtgccctggc ccaccctcgt gaccaccctg   1020
acctacggcg tgcagtgctt cagccgctac cccgaccaca tgaagcagca cgacttcttc   1080
aagtccgcca tgcccgaagg ctacgtccag gagcgcacca tcttcttcaa ggacgacggc   1140
aactacaaga cccgcgccga ggtgaagttc gagggcgaca ccctggtgaa ccgcatcgag   1200
ctgaagggca tcgacttcaa ggaggacggc aacatcctgg gcacaagct ggagtacaac   1260
tacaacagcc acaacgtcta tatcatggcc gacaagcaga agaacggcat caaggtgaac   1320
ttcaagatcc gccacaacat cgaggacggc agcgtgcagc tcgccgacca ctaccagcag   1380
aacacccca tcggcgacgg ccccgtgctg ctgcccgaca accactacct gagcacccag   1440
```

```
tccgccctga gcaaagaccc caacgagaag cgcgatcaca tggtcctgct ggagttcgtg    1500
accgccgccg ggatcactct cggcatggac gagctgtaca agtaagctgc cttctgcggg    1560
gcttgccttc tggccatgcc cttcttctct cccttgcacc tgtacctctt ggtctttgaa    1620
taaagcctga gtaggaagtg agggtctaga actagtgtcg acgcaagggt tcgatcccta    1680
ccggttagta atgagtttaa acggggggagg ctaactgaaa cacggaagga gacaataccg    1740
gaaggaaccc gcgctatgac ggcaataaaa agacagaata aaacgcacgg gtgttgggtc    1800
gtttgttcat aaacgcgggg ttcggtccca gggctggcac tctgtcgata ccccaccgag    1860
accccattgg ggccaatacg cccgcgtttc ttccttttcc caccccacc ccccaagttc     1920 gggtgaaggc ccagggctcg cagccaacgt cggggcggca ggccctgcca tagcagatct    1980
gcgcagctgg ggctctaggg ggtatcccca cgcgccctgt agcggcgcat taagcgcggc    2040
gggtgtggtg gttacgcgca gcgtgaccgc tacacttgcc agcgccctag cgcccgctcc    2100
tttcgctttc ttcccttcct ttctcgccac gttcgccggc tttccccgtc aagctctaaa    2160
tcggggcatc cctttagggt tccgatttag tgctttacgg cacctcgacc ccaaaaaact    2220
tgattagggt gatggttcac gtagtgggcc atcgccctga tagacggttt ttcgcccttt    2280
gacgttggag tccacgttct ttaatagtgg actcttgttc caaactggaa caacactcaa    2340
ccctatctcg gtctattctt ttgatttata agggattttg gggatttcgg cctattggtt    2400
aaaaaatgag ctgatttaac aaaaatttaa cgcgaattaa ttctgtggaa tgtgtgtcag    2460
ttagggtgtg gaaagtcccc aggctcccca gcaggcagaa gtatgcaaag catgcatctc    2520
aattagtcag caaccaggtg tggaaagtcc ccaggctccc cagcaggcag aagtatgcaa    2580
agcatgcatc tcaattagtc agcaaccata gtcccgcccc taactccgcc catcccgccc    2640
ctaactccgc ccagttccgc ccattctccg ccccatggct gactaatttt ttttatttat    2700
gcagaggccg aggccgcctc tgcctctgag ctattccaga agtagtgagg aggcttttt     2760 ggaggcctag gcttttgcaa aaagctcccg ggagcttgta tatccatttt cggatctgat    2820
caagagacag gatgaggatc gtttcgcatg attgaacaag atggattgca cgcaggttct    2880
ccggccgctt gggtggagag gctattcggc tatgactggg cacaacagac aatcggctgc    2940
tctgatgccg ccgtgttccg gctgtcagcg caggggcgcc cggttctttt tgtcaagacc    3000
gacctgtccg gtgccctgaa tgaactgcag gacgaggcag cgcggctatc gtggctggcc    3060
acgacgggcg ttccttgcgc agctgtgctc gacgttgtca ctgaagcggg aagggactgg    3120
ctgctattgg gcgaagtgcc ggggcaggat ctcctgtcat ctcaccttgc tcctgccgag    3180
aaagtatcca tcatggctga tgcaatgcgg cggctgcata cgcttgatcc ggctacctgc    3240
ccattcgacc accaagcgaa acatcgcatc gagcgagcac gtactcggat ggaagccggt    3300
cttgtcgatc aggatgatct ggacgaagag catcaggggc tcgcgccagc cgaactgttc    3360
gccaggctca aggcgcgcat gcccgacggc gaggatctcg tcgtgaccca tggcgatgcc    3420
tgcttgccga atatcatggt ggaaaatggc cgcttttctg gattcatcga ctgtggccgg    3480
ctgggtgtgg cggaccgcta tcaggacata gcgttggcta cccgtgatat tgctgaagag    3540
cttggcggcg aatgggctga ccgcttcctc gtgctttacg gtatcgccgc tcccgattcg    3600
cagcgcatcg ccttctatcg ccttcttgac gagttcttct gagcgggact ctggggttcg    3660
cgaaatgacc gaccaagcga cgcccaacct gccatcacga gatttcgatt ccaccgccgc    3720
cttctatgaa aggttgggct tcggaatcgt tttccgggac gccggctgga tgatcctcca    3780
gcgcggggat ctcatgctgg agttcttcgc ccaccccaac ttgtttattg cagcttataa    3840
```

```
tggttacaaa taaagcaata gcatcacaaa tttcacaaat aaagcatttt tttcactgca    3900
ttctagttgt ggtttgtcca aactcatcaa tgtatcttat catgtctgta taccgtcgac    3960
ctctagctag agcttggcgt aatcatggtc atagctgttt cctgtgtgaa attgttatcc    4020
gctcacaatt ccacacaaca tacgagccgg aagcataaag tgtaaagcct ggggtgccta    4080
atgagtgagc taactcacat taattgcgtt gcgctcactg cccgctttcc agtcgggaaa    4140
cctgtcgtgc cagctgcatt aatgaatcgg ccaacgcgcg gggagaggcg gtttgcgtat    4200
tgggcgctct tccgcttcct cgctcactga ctcgctgcgc tcggtcgttc ggctgcggcg    4260
agcggtatca gctcactcaa aggcggtaat acggttatcc acagaatcag gggataacgc    4320
aggaaagaac atgtgagcaa aaggccagca aaaggccagg aaccgtaaaa aggccgcgtt    4380
gctggcgttt ttccataggc tccgcccccc tgacgagcat cacaaaaatc gacgctcaag    4440
tcagaggtgg cgaaacccga caggactata agataccag gcgtttcccc ctggaagctc    4500
cctcgtgcgc tctcctgttc cgaccctgcc gcttaccgga tacctgtccg cctttctccc    4560
ttcgggaagc gtggcgcttt ctcaatgctc acgctgtagg tatctcagtt cggtgtaggt    4620
cgttcgctcc aagctgggct gtgtgcacga accccccgtt cagcccgacc gctgcgcctt    4680
atccggtaac tatcgtcttg agtccaaccc ggtaagacac gacttatcgc cactggcagc    4740
agccactggt aacaggatta gcagagcgag gtatgtaggc ggtgctacag agttcttgaa    4800
gtggtggcct aactacggct acactagaag gacagtattt ggtatctgcg ctctgctgaa    4860
gccagttacc ttcggaaaaa gagttggtag ctcttgatcc ggcaaacaaa ccaccgctgg    4920
tagcggtggt ttttttgttt gcaagcagca gattacgcgc agaaaaaaag gatctcaaga    4980
agatcctttg atcttttcta cggggtctga cgctcagtgg aacgaaaact cacgttaagg    5040
gattttggtc atgagattat caaaaaggat cttcacctag atcctttta attaaaaatg    5100
aagttttaaa tcaatctaaa gtatatatga gtaaacttgg tctgacagtt accaatgctt    5160
aatcagtgag gcacctatct cagcgatctg tctatttcgt tcatccatag ttgcctgact    5220
ccccgtcgtg tagataacta cgatacggga gggcttacca tctggcccca gtgctgcaat    5280
gataccgcga gacccacgct caccggctcc agatttatca gcaataaacc agccagccgg    5340
aagggccgag cgcagaagtg gtcctgcaac tttatccgcc tccatccagt ctattaattg    5400
ttgccgggaa gctagagtaa gtagttcgcc agttaatagt ttgcgcaacg ttgttgccat    5460
tgctacaggc atcgtggtgt cacgctcgtc gtttggtatg gcttcattca gctccggttc    5520
ccaacgatca aggcgagtta catgatcccc catgttgtgc aaaaaagcgg ttagctcctt    5580
cggtcctccg atcgttgtca gaagtaagtt ggccgcagtg ttatcactca tggttatggc    5640
agcactgcat aattctctta ctgtcatgcc atccgtaaga tgcttttctg tgactggtga    5700
gtactcaacc aagtcattct gagaatagtg tatgcggcga ccgagttgct cttgcccggc    5760
gtcaatacgg gataataccg cgccacatag cagaacttta aaagtgctca tcattggaaa    5820
acgttcttcg gggcgaaaac tctcaaggat cttaccgctg ttgagatcca gttcgatgta    5880
acccactcgt gcacccaact gatcttcagc atcttttact ttcaccagcg tttctgggtg    5940
agcaaaaaca ggaaggcaaa atgccgcaaa aaagggaata aggcgacac ggaaatgttg    6000
aatactcata ctcttccttt tcaatatta ttgaagcatt tatcagggtt attgtctcat    6060
gagcggatac atatttgaat gtatttagaa aaataaacaa ataggggttc cgcgcacatt    6120
tccccgaaaa gtgccacctg acgtcgacgg atcgggagat ctcccgatcc cctatggtcg    6180
actctcagta caatctgctc tgatgccgca tagttaagcc agtatctgct ccctgcttgt    6240
```

```
gtgttggagg tcgctgagta gtgcgcgagc aaaatttaag ctacaacaag gcaaggcttg    6300
accgacaatt gcatgaagaa tctgcttagg                                     6330

<210> SEQ ID NO 6
<211> LENGTH: 1878
<212> TYPE: DNA
<213> ORGANISM: Artificial Sequence
<220> FEATURE:
<223> OTHER INFORMATION: linear DNA

<400> SEQUENCE: 6
ttcgcgatgt acgggccaga tatacgcgtt gacattgatt attgactagt tattaatagt      60
aatcaattac ggggtcatta gttcatagcc catatatgga gttccgcgtt acataactta     120
cggtaaatgg cccgcctggc tgaccgccca acgacccccg cccattgacg tcaataatga     180
cgtatgttcc catagtaacg ccaataggga ctttccattg acgtcaatgg gtggagtatt     240
tacggtaaac tgcccacttg gcagtacatc aagtgtatca tatgccaagt acgcccccta     300
ttgacgtcaa tgacggtaaa tggcccgcct ggcattatgc ccagtacatg accttatggg     360
actttcctac ttggcagtac atctacgtat tagtcatcgc tattaccatg gtgatgcggt     420
tttggcagta catcaatggg cgtggatagc ggtttgactc acggggattt ccaagtctcc     480
accccattga cgtcaatggg agtttgtttt ggcaccaaaa tcaacgggac tttccaaaat     540
gtcgtaacaa ctccgcccca ttgacgcaaa tgggcggtag gcgtgtacgg tgggaggtct     600
atataagcag agctcgttta gtgaaccgtc agatcgcctg gagacgccat ccacgctgtt     660
ttgacctcca tagaagacac cgggaccgat ccagcctccg gactctagag gatcgaaccc     720
ttttggaccc tcgtacagaa gctaatacga ctcactatag ggaaataaga gagaaaagaa     780
gagtaagaag aaatataaga gccaccatgg tgagcaaggg cgaggagctg ttcaccgggg     840
tggtgcccat cctggtcgag ctggacgcg acgtaaacgg ccacaagttc agcgtgtccg     900
gcgagggcga gggcgatgcc acctacggca agctgaccct gaagttcatc tgcaccaccg     960
gcaagctgcc cgtgccctgg cccaccctcg tgaccaccct gacctacggc gtgcagtgct    1020
tcagccgcta ccccgaccac atgaagcagc acgacttctt caagtccgcc atgcccgaag    1080
gctacgtcca ggagcgcacc atcttcttca aggacgacgg caactacaag acccgcgccg    1140
aggtgaagtt cgaggcgac accctggtga accgcatcga gctgaagggc atcgacttca    1200
aggaggacgg caacatcctg ggcacaagc tggagtacaa ctacaacagc cacaacgtct    1260
atatcatggc cgacaagcag aagaacggca tcaaggtgaa cttcaagatc cgccacaaca    1320
tcgaggacgg cagcgtgcag ctcgccgacc actaccagca gaacaccccc atcggcgacg    1380
gccccgtgct gctgcccgac aaccactacc tgagcaccca gtccgccctg agcaaagacc    1440
ccaacgagaa gcgcgatcac atggtcctgc tggagttcgt gaccgccgcc gggatcactc    1500
tcggcatgga cgagctgtac aagtaagctg ccttctgcgg ggcttgcctt ctggccatgc    1560
ccttcttctc tcccttgcac ctgtacctct tggtctttga ataaagcctg agtaggaagt    1620
gagggtctag aactagtgtc gacgcaaggg ttcgatccct accggttagt aatgagttta    1680
aacgggggag gctaactgaa acacggaagg agacaatacc ggaaggaacc cgcgctatga    1740
cggcaataaa aagacagaat aaaacgcacg ggtgttgggt cgtttgttca taaacgcggg    1800
gttcggtccc agggctggca ctctgtcgat accccaccga acccccattg gggccaatac    1860
gcccgcgttt cttcctttt                                                1878
```

-continued

```
<210> SEQ ID NO 7
<211> LENGTH: 18
<212> TYPE: PRT
<213> ORGANISM: Artificial Sequence
<220> FEATURE:
<223> OTHER INFORMATION: p53 peptide
<220> FEATURE:
<221> NAME/KEY: 1
<222> LOCATION: (3)..(3)
<223> OTHER INFORMATION: Xaa is Qln
<220> FEATURE:
<221> NAME/KEY: 2
<222> LOCATION: (5)..(6)
<223> OTHER INFORMATION: Xaa is Qln
<220> FEATURE:
<221> NAME/KEY: 3
<222> LOCATION: (9)..(9)
<223> OTHER INFORMATION: Xaa is a non-natural amino acid introduced with
      an alkyne functional group wherein 4-pentynoic acid is introduced
      at a side chain of D-Lys
<220> FEATURE:
<221> NAME/KEY: 4
<222> LOCATION: (16)..(16)
<223> OTHER INFORMATION: Xaa is a non-natural amino acid introduced with
      an azide functional group and denotes 2-amino-5-azido-pentanoic
      acid
<220> FEATURE:
<221> NAME/KEY: 5
<222> LOCATION: (17)..(17)
<223> OTHER INFORMATION: Xaa is Qln

<400> SEQUENCE: 7

Gly Gly Xaa Ser Xaa Xaa Thr Phe Xaa Asn Leu Trp Arg Leu Leu Xaa
1               5                   10                  15

Xaa Asn
```

PHYSIOLOGICALLY ACTIVE SUBSTANCE CARRIER

CROSS-REFERENCE TO RELATED APPLICATION AND CLAIM OF PRIORITY

The present application is a continuation of U.S. patent application Ser. No. 16/483,830, filed Aug. 6, 2019, which is a National Phase application under 35 U.S.C. § 371 of International Application No. PCT/KR2018/001617, filed Feb. 6, 2018, which claims priority to the benefit of U.S. Patent Application No. 62/455,148 filed in the US Patent Office on Feb. 6, 2017 and Korean Patent Application No. 10-2018-0014842 filed in the Korean Intellectual Property Office on Feb. 6, 2018, the entire contents of which are incorporated herein by reference.

BACKGROUND

1. Field

The present invention relates to a physiologically active substance ("bioactive substance") carrier.

2. Description of the Related Art

A drug delivery system refers to a pharmaceutical technology able to efficiently deliver a desired amount of drug, for example, proteins, nucleic acids or other low molecular weight compounds while minimizing side effects of existing drugs and maximizing efficacy and effects thereof The above-described technology enabling reduction of costs and time required for development of novel drugs has recently planted itself as an area of applications in high technology that creates newly added values in medical science, while combining with nanotechnology. Further, since the late 1980s, technology advanced countries such as US and Japan have concentrated on development of the drug delivery system as well as novel drugs in cooperation with businesses, including pharmaceutical companies who play a key role.

Until now, viral genes, recombinant proteins, liposome, cationic polymers and various types of nanoparticles and nano-materials have been used for drug delivery into animal cells. However, it has been found that many cationic liposomes and cationic polymers have strong toxicity to cells, such that they are unsuitable for application to clinical practice. Further, for stable membrane permeation of a nucleic acid, a method of chemically modifying a main chain in the nucleic acid has been also attempted. However, such a method is expensive, takes a long period of time and needs a labor-intensive process, hence not being suitable for clinical applications. There was a significant attempt to develop a drug delivery system (DDS) using various types of nanoparticles, including quantum dots, magnetic particles or gold nanoparticles. For example, there was a related research such as "image diagnostic drug delivery carrier using porous silicon particles and a manufacturing method thereof (Korean Patent Laid-Open Publication No. 2010-0117433)." However, such particles have disadvantages of toxicity to cells, a structure not susceptible to introduction of biomolecules such as nucleic acids, and low introduction efficiency into cells.

In order to study functions or intracellular delivery of a bioactive substance in the cells, an efficient delivery system is required. However, development of a delivery system for general purpose that can deliver a wide range of bioactive substances, a system for accepting and delivering a large amount of drug, a sustained drug release system, etc. is still incomplete.

SUMMARY

It is an object of the present invention to provide a bioactive substance carrier which is used for general purpose.

Another object of the present invention is to provide a bioactive substance carrier, which can deliver a variety of bioactive substances in a sustained manner.

1. A bioactive substance carrier, comprising: a bioactive substance; and a porous silica particle supporting the bioactive substance, having a plurality of pores with a diameter of 5 nm to 100 nm, and having 't' of not less than 24, at which a ratio of absorbance measured by Equation 1 below is ½:

$$At/A0 \qquad [\text{Equation 1}]$$

wherein $A0$ denotes an absorbance of the porous silica particle measured after putting 5 ml of a suspension including 1 mg/ml of the porous silica particle in a cylindrical permeable membrane having pores with a diameter of 50 kDa, wherein 15 ml of a solvent in contact with the permeable membrane and substantially identical to the suspension is present outside the permeable membrane, inner and outer portions of the permeable membrane are horizontally agitated at 37° C. and 60 rpm, the suspension has pH 7.4, and wherein $At$ denotes an absorbance of the porous silica particle measured T hour after the measurement of $A0$.

2. The bioactive substance carrier of the above 1, wherein the suspension is one or more selected from the group consisting of phosphate buffered saline (PBS) and simulated body fluid (SBF).

3. The bioactive substance carrier of the above 1, wherein At in Equation 1 is measured in an environment in which the solvent outside the permeable membrane is changed at a predetermined time period.

4. The bioactive substance carrier of the above 1, wherein the 't' ranges from 24 to 120.

5. The bioactive substance carrier of the above 1, wherein the porous silica particle is biodegradable.

6. The bioactive substance carrier of the above 1, wherein the porous silica particle has "t" of 70 to 120, at which a ratio of absorbance measured by Equation 1 is ⅕.

7. The bioactive substance carrier of the above 1, wherein the porous silica particle has "t" of 130 to 220, at which a ratio of absorbance measured by Equation 1 is 1/20.

8. The bioactive substance carrier of the above 1, wherein a Pearson correlation coefficient between the ratio of absorbance measured by Equation 1 and "t" is 0.8 or more.

9. The bioactive substance carrier of the above 1, wherein the pore diameter ranges from 7 nm to 30 nm.

10. The bioactive substance carrier of the above 1, wherein the porous silica particle has a spherical shape.

11. The bioactive substance carrier of the above 1, wherein an average diameter of the porous silica particle ranges from 150 nm to 1000 nm.

12. The bioactive substance carrier of the above 1, wherein the porous silica particle has a BET surface area in a range of 200 $m^2/g$ to 700 $m^2/g$.

13. The bioactive substance carrier of the above 1, wherein the porous silica particle has a BET surface area in a range of 300 $m^2/g$ to 450 $m^2/g$.

14. The bioactive substance carrier of the above 1, wherein a volume of the porous silica particle per gram ranges from 0.7 ml to 2.2 ml.

15. The bioactive substance carrier of the above 1, wherein a volume of the porous silica particle per gram ranges from 1.0 ml to 2.0 ml.

16. The bioactive substance carrier of the above 1, wherein the porous silica particles has a hydrophilic substituent or hydrophobic substituent on an outer surface of the particle or inside the pore.

17. The bioactive substance carrier of the above 1, wherein the porous silica particles is positively or negatively charged on the outer surface of the particle or inside the pore at neutral pH.

18. The bioactive substance carrier of the above 1, wherein the bioactive substance is non-soluble, and the porous silica particle has a hydrophobic substituent on the outer surface of the particle or inside the pore.

19. The bioactive substance carrier of the above 1, wherein the bioactive substance is non-soluble, and the porous silica particle has a hydrophobic substituent inside the pore and a hydrophilic substituent on the outer surface of the particle.

20. The bioactive substance carrier of the above 1, wherein the bioactive substance is negatively charged at neutral pH, and the porous silica particle is positively charged on the outer surface of the particle or inside the pore at neutral pH.

21. The bioactive substance carrier of the above 1, wherein the bioactive substance is positively charged at neutral pH, and the porous silica particle is negatively charged on the outer surface of the particle or inside the pore at neutral pH.

22. A bioactive substance carrier, comprising: a bioactive substance; and a spherical porous silica particle supporting the bioactive substance, having a plurality of pores with a particle diameter of 150 nm to 500 nm and a diameter of 7 nm to 30 mm, and having 't' in a range of 24 to 120, at which a ratio of absorbance measured by Equation 2 below is ½:

$$At/A0 \quad \text{[Equation 2]}$$

wherein A0 denotes an absorbance of porous silica particles measured after putting 5 ml of a suspension including 1 mg/ml of the porous silica particle in a cylindrical permeable membrane having pores with a diameter of 50 kDa, wherein 15 ml of a solvent in contact with the permeable membrane and substantially identical to the suspension is present outside the permeable membrane, inner and outer portions of the permeable membrane are horizontally agitated at 37° C. and 60 rpm, the suspension is PBS or SBF and has pH 7.4, and wherein At denotes an absorbance of the porous silica particles measured 't' hour after the measurement of A0.

23. The bioactive substance carrier of the above 22, wherein the porous silica particle has a BET surface area in a range of 300 m²/g to 450 m²/g, and a volume per g in a range of 1.0 ml to 2.0 ml.

24. The bioactive substance carrier of the above 22, wherein the bioactive substance is non-soluble, and the porous silica particle has a hydrophobic substituent on an outer surface of the particle or inside the pore.

25. The bioactive substance carrier of the above 22, wherein the bioactive substance is non-soluble, and the porous silica particle has a hydrophobic substituent inside the pore and a hydrophilic substituent on the outer surface of the particle.

26. The bioactive substance carrier of the above 22, wherein the bioactive substance is negatively charged at neutral pH, and the porous silica particle is positively charged on the outer surface of the particle or inside the pore at neutral pH.

27. The bioactive substance carrier of the above 22, wherein the bioactive substance is positively charged at neutral pH, and the porous silica particle is negatively charged on the outer surface of the particle or inside the pore at neutral pH.

28. A method for manufacturing a bioactive substance carrier, comprising coming into contact a porous silica particle with a bioactive substance in a solvent.

29. The method of the above 28, wherein the solvent is one or more selected from the group consisting of water, chloroform, methylene chloride, carbon tetrachloride, 1,2-dichloroethane, dichloroethylene, trichloroethylene, perchloroethylene, dichloropropane, amyl chloride, 1,2-dibromoethane, acetone, methyl isobutylketone, cyclohexanone, benzene, toluene, xylene, N,N-dimethyl formamide, N,N-dibutylformamide, N,N-dimethylacetamide, N-methylpyrrolidone, methanol, ethanol, propanol, butanol, PBS, SBF, borate-buffered saline and tris-buffered saline.

30. The method of the above 28, wherein a ratio by weight of the porous silica particle to the bioactive substance is 1:0.05 to 0.8.

31. A method for delivery of a bioactive substance, comprising parenterally administering the bioactive substance carrier according to any one of claims 1 to 27 to an individual subject.

32. The method of the above 31, wherein the parenteral administration is intra-orbital, intra-ocular, infusion, intra-arterial, intra-articular, intra-cardiac, intra-dermal, intra-muscular, intra-peritoneal, intra-pulmonary, intra-spinal, intra-sternal, intra-thecal, intra-uterine, intravenous, subarachnoid, subcapsular, subcutaneous, transmucosal or transorgan administration.

The bioactive substance carrier of the present invention may include porous silica particles supporting the bioactive substance, which are slowly degraded in vivo, thus delivering a drug in a sustained manner.

The bioactive substance carrier of the present invention may include porous silica particles supporting (i.e., carrying) the bioactive substance, which are completely degraded in vivo, thus to completely deliver the supported bioactive substance to a living body.

The bioactive substance carrier of the present invention may be parenterally administered.

The bioactive substance carrier of the present invention may deliver a variety of drugs in a sustained manner.

DETAILED DESCRIPTION

Figure 1:
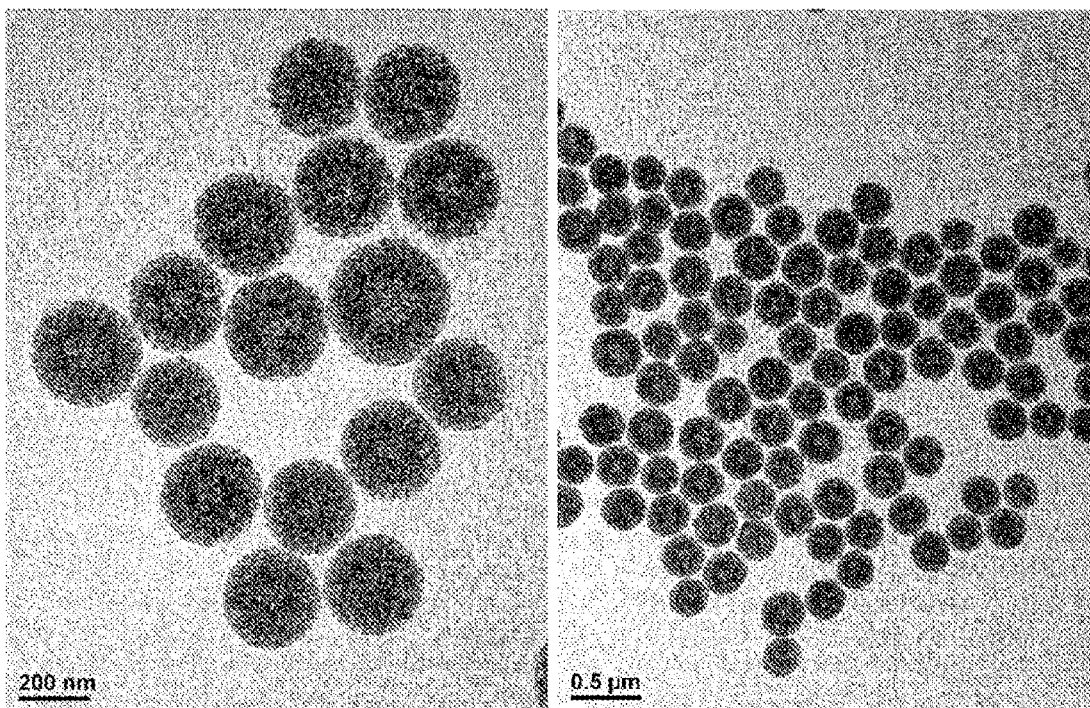
FIG. 1 is microphotographs showing porous silica particles according to one embodiment of the present invention.

The bioactive substance carrier of the present invention may include: a bioactive substance; and porous silica particles supporting the bioactive substance and having a plurality of pores with a diameter of 5 nm to 100 nm.

Bioactive Substance

The bioactive substance is a physiologically active substance/biofunction control substance supported on the porous silica particles and delivered to an individual object to exhibit activity, which may play a role of a therapeutically active agent capable of affording direct, indirect, therapeutic, physiological and/or pharmacological effects to a human or animal organism.

Such a therapeutically active agent as described above may include, for example, general medicine, medicament, drug or pro-drug, target groups, or drug or pro-drug containing a target group.

More particularly, the therapeutically active agent may include, for example: cardiovascular drugs, in particular, anti-hypertensive agents (e.g., calcium channel blockers or calcium antagonists) and antiarrhythmics; congestive heart failure medicine; muscle contractants; vasodilators; ACE inhibitors; diuretics; deoxidation anhydrase inhibitors; cardiac glycosides; phosphodiesterase inhibitors; blockers; β-blockers; sodium channel blockers; potassium channel blockers; β-adrenergic agonists; platelet inhibitors; angiotensin II antagonists; anticoagulants; thrombolytic agents; bleeding drugs; anemia drugs; thrombin inhibitors; antiparasitics; antibacterial agents; anti-inflammatory agents, in particular, nonsteroidal anti-inflammatory agents (NSAIDs), more in particular, COX-2 inhibitors; steroidal anti-inflammatory drugs; prophylactic anti-inflammatory agents; antiglaucoma agents; mast cell stabilizers; mydriatics; drugs affecting the respiratory system; allergic rhinitis drugs; alpha-adrenergic antagonists; corticosteroids; chronic obstructive pulmonary pills; xanthine-oxidase inhibitors; anti-arthritis agents; gout therapeutic agents; multipotent drugs and multipotent drug antagonists; anti-tuberculosis agents; antifungal agents; antigen pesticide; helminthics; anti-viral agents, in particular, anti-viral agents against respiratory, herpes, cytomegalovirus, human immunodeficiency virus and hepatitis infection; Kaposi's sarcoma and leukemia treatment agents; pain management agents, in particular, anesthetics and analgesics, opioids including opioid receptor agonists, opioid receptor partial agonists, opioid antagonists, opioid receptor mixed agonist-antagonists, etc.; neuroleptics; sympathomimetics; adrenergic antagonists; neurotransmission drugs that affect absorption and emission of neurotransmitter; anticholinergic stimulants; anti hemorrhoid treatment agents; radiation or preventive or treatment agents with therapeutic effect of chemotherapy; adipogenics; fat reduction agents; anti-obesity drugs such as lipase inhibitors; sympathomimetic agents; gastric ulcer and inflammatory therapeutic agents such as proton pump inhibitors; prostaglandins; VEGF inhibitors; anti-dyslipidemia agents, in particular, statins; drugs affecting the central nervous system (CNS) such as antipsychotic, antiepileptic and anti-seizure agents (anticonvulsants), mental active agents, stimulants, anti-anxiety agents and hypnotics; antidepressants; antiparkinson agents; hormone and fragments thereof such as sexual hormones; growth hormone antagonists; gonadotropin releasing hormone and analogs thereof; steroid hormones and antagonists thereof; selective estrogen modulator; growth factors; anti-diabetic agents such as insulin, insulin fragments, insulin analogs, glucagon-like peptides and hypoglycemic agents; H1, H2, H3 and H4 antihistamine; peptides, proteins, polypeptides, nucleic acids, and oligonucleotide drugs; analogs, fragments and variants such as natural proteins, polypeptides, oligonucleotides and nucleic acids; drugs used for treatment of migraine; antiasthmatics; cholinergic antagonists; glucocorticoids; androgens; antiandrogens; adrenocorticoid biosynthesis inhibitors; osteoporosis treatment agents such as biphosphonate; antithyroids; sunscreens, UV preventive protectants and filters; cytokine antagonists; antitumor agents; anti-Alzheimer's agents; HMGCoA reductase inhibitors; fibrates; cholesterol absorption inhibitors; HDL cholesterol-elevating agents; triglyceride reducing agents; anti-aging or anti-wrinkle agents; proteins such as collagen and elastin, antimicrobial agents; anti-acne agents; antioxidants; hair treatments and skin whitening agents; variants of human apolipidoprotein; precursor molecules for generation of hormones; proteins and peptides thereof; amino acids; plant extracts such as grape seed extract; DHEA; isoflavones; nutrients including vitamins, phytosterols and iridoid glycosides, sesquicarbonate lactones, terpenes, phenolic glycosides, triterpenes, hydroquinone derivatives, phenylalkanone; antioxidants such as retinol and other retinoids including retinoic acid and coenzyme Q10; omega-3 fatty acids; glucosamine; nucleic acid, oligonucleotide, antisense medicine; enzyme; coenzyme; cytokine analogs; cytokine agonists; cytokine antagonists; immunoglobulins; antibodies; antibody medicine; gene therapy agents; lipoprotein; erythropoietin; vaccines; small molecule therapeutic agents for treatment or prevention of human and animal diseases such as allergy/asthma, arthritis, cancer, diabetes, growth disorders, cardiovascular disorders, inflammation, immune dysfunction, baldness, pain, ophthalmologic diseases, epilepsy, gynecological disorders, CNS disorders, viral infections, bacterial infections, parasitic infections, G1 diseases, obesity and blood diseases, etc., but it is not limited thereto.

The therapeutically active agents may be additional active agents include, for example, erythropoietine (EPO), thrombopoietin, cytokines such as interleukine (including IL-1 to IL-17), insulin, insulin-like growth factors (including IGF-1 and IGF-2), epidermal growth factor (EGF), transforming growth factors (including TGF-alpha and TGF-beta), human growth hormone, transferrine, low density lipoproteins, high density lipoproteins, leptine, VEGF, PDGF, ciliary neurotrophic factor, prolactine, adrenocorticotropic hormone (ACTH), calcitonine, human chrorionic gonadotropin, cortisol, estradiol, follicle stimulating hormones (FSH), thyroid-stimulating hormone (TSH), luteinizing hormone (LH), toxin including progesterone, testosterone, ricine, etc.

The therapeutically active agent may be selected from a drug group for treatment of oncological diseases and cell or tissue transformation. Suitable therapeutic formulation may include antineoplastic agents, for example: alkyl sulfonate such as busulfan, improsulfan, pipSulfane, etc., alkylating agents including benzodepa, carboquone, meturedepa, aziridine such as uredepa, etc.; altretamine, triethylene melamine, triethylene phosphoramide, triethylene thiophosphoramide, ethyleneimine such as trimethylolmelamine, and methyl melamine; chlorambucil, chlornaphazine, cyclophosphamide, estramustine, ifosfamide, mechlorethamine, mechlorethamine oxide, mechlorethaminoxide hydrochloride, melphalan, novembichin, phenesterine, prednimustine, trofosfamide, so-called nitrogen mustards such as uracil mustard; nitroso-urea compounds such as carmustine, chlorozotocin, fotenmustine, lomustine, nimustine, ranimustine; dacarbazine, mannomustine, mitobranitol, mitolactol; pipobroman; sorafenib; doxorubicin and cis-platinum and derivatives thereof, and any combination and/or derivatives of the above substances.

The therapeutically active agent may be selected from the group consisting of antiviral agents and antibacterial agents, such as aclacinomycin, actinomycin, anthramycin, azaserin, bleomycin, cuctinomycin, carubicin, carzinophilin, chromomycin, ductinomycin, daunorbicin, 6-diazo-5-oxn-1-norieucin, doxorubicin, epirubicin, mitomycin, mycophenolsaure, mogalumycin, olivomycin, peplomycin, plicamycin, porfiromycin, puromycin, streptonigrin, streptozocin, tubercidine, ubenimex, zinostatin, zorubicin, aminoglycoside, polyene or macrolid-antibiotics, and any combination and/or derivatives of the above substances.

The therapeutically active agent may be selected from: endostatin, angiostatin, interferone, platelet factor 4 (PF4), thrombospondin, transforming growth factor beta, tissue inhibitor of the metalloproteinase-1, -2 and -3 (TIMP-1, -2 and -3), TNP-470, marimastat, neovastat, BMS-275291, COL-3, AG3340, thalidomide, squalamine, combrestastatin, radio-sensitizer drugs such as SU5416, SU6668, IFN-[alpha], EMD121974, CAI, IL-12 and IM-862, steroidal or non-steroidal anti-inflammatory drugs, or formulations for angiogenesis, and combinations and/or derivatives of the above substances.

The therapeutically active agent may be selected from the group including nucleic acids. In this regard, for example, in order to afford gene therapeutic or antisense effects, the term "nucleic acid" may include oligonucleotide containing at least two nucleotides linked together through a covalent bond. The nucleic acid preferably has a phosphodiester bond. Alternatively, analogues having different backbones, respectively, are also included. The analogues may include a backbone, for example, phosphoramide, phosphorothioate, phosphorodithioate, O-methyl phosphoroamidit compound, and peptide-nucleic acid-backbone and compounds thereof. Other analogs may have an ionic backbone, a non-ionic backbone, or a non-ribose-backbone. The nucleic acid having one or more carbocyclic sugar may be suitable as a nucleic acid used in the present invention. Other than the selection of nucleic acids and nucleic acid analogs known in the art, naturally generated nucleic acids and nucleic acid analogs or any combination of mixtures of the nucleic acids and nucleic acid analogs may also be applied.

The therapeutically active agent may include, for example, everolimus, tacrolimus, sirolimus, mycofenolatemofetil, rapamycin, paclitaxel, actinomycine D, angiopeptin, batimastate, estradiol, VEGF, statine, etc., and their derivatives and analogs, which are useable as anti-migratory, anti-proliferative, immune-suppressive, anti-inflammatory or re-endotheliating agent.

The therapeutically active agent may include opioid receptors, agonists and antagonists, compounds showing agonist/antagonist mixed activity and compounds showing partial agonist activity, for example, morphine, depot morphine, atropine, diacetyl morphine, hydromorphine, oxymorphone, levorphanol, methadone, levomethadyl, meperidine, fentanyl, sufentanil, alfentanil, codeine, hydrocodone, oxycodone, thebaine, desomorphine, nicomorphine, dipropanoyl morphine, benzyl morphine, ethyl morphine, pethidine, methadone, tramadol, dextropropoxyphene; naloxsone and naltrexone; buprenorphine, nalbuphine, butorphanol, petazocine and ethylketocyclazocine.

The therapeutically active agents and a combination thereof may be selected from, for example: heparin, synthetic heparin analogs (e.g., fondaparinux), hirudin, antithrombin III, drotrecogin alpha; fibrinolytics such as alteplase, plasmin, lysokinase, factor VIIa, prourokinase, urokinase, anistreplase, streptokinase, etc.; platelet aggregation inhibitors such as acetylsalicylic acid [aspirine], ticlopidine, clopidogrel, abciximab, dextran, etc.; corticosteroids such as alclometasone, amcinonide, augmented betamethasone, beclomethasone, betamethasone, budesonide, cortisone, clobetasol, clocortolone, desonide, desoximetasone, dexamethasone, fluocinolone, fluocinonide, flurandrenolide, flunisolide, fluticasone, halcinonide, halobetasol, hydrocortisone, methylprednisolone, momethasone, prednicarbate, prednisone, prednisolone, triamcinolone, etc.; so-called non-steroidal anti-inflammatory drugs (NSAIDs) such as diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, oxaprozin, piroxicam, salsalate, sulindac, tolmetin, celecoxib, rofecoxib, etc.; cytostatics, including alkaloids such as vinblastine, vincristine, etc. and podophyllum toxin, etc.; cytotoxic antibiotics such as daunorbicin, doxorubicin, other anthracyclines and related substances, bleomycin, mitomycin, etc.; antimetabolites, such as folic acid analogs, purine analogs or pyrimidine analogs, etc.; paclitaxel, docetaxel, sirolumus; platinum compounds such as carboplatin, cisplatin or oxaliplatin, etc.; amsacrin, irinitecan, imatinib, topotecan, nterferone-alpha 2a, interferone-alpha 2b, hydroxycarbide, miltefosine, pentostatin, porfimer, aldesleukin, bexaroten, tretinoin; antiandrogen and antiestrogen; antiarrhythmics, including quinidine type antiarrhythmics, in particular, type I antiarrhythmics such as quinidine, diisopyramide, ajmaline, prajmalium bitartrate, detajmium bitartrate, etc.; lidocaine type antiarrhythmics, for example, lidocaine, mexiletin, phenytoin, tocainid, etc.; Ic type antiarrhythmics, for example, propafenon, flecainid (acetate), etc.; class II antiarrhythmics beta-receptor blocker such as metoprolol, esmolol, propranolol, atenolol, oxprenolol, etc.; type III antiarrhythmics such as amiodarone, sotalol, etc.; type IV antiarrhythmics such as diltiazem, verapamil, gallopamil, etc.; other antharrhythmics such as adenosine, orciprenaline, ipratropium bromide, etc.; formulations to stimulate angiogenesis in myocardium such as vascular endothelial growth factor (VEGF), basic fibroblast growth factor (bFGF), non-viral DNA, viral DNA, endothelial growth factor, etc.; FGF-1, FGF-2, VEGF, TGF; antibiotics, monoclonal antibodies, anticalin; stem cells, endothelial progenitor cells (EPC); digitalis glycosides such as acetyl digoxin/methyl digoxin, digitoxin, digoxin, etc.; cardiac glycoside such as ouabain, proscillaridin, etc.; antihypertensive agents, for example, methyldopa, imidazoline receptor agonists as CNS active antiadrenergic substance, etc.; dihydropiridine type calcium channel blocker such as nifedipine, nitrendipine, etc.; ACE inhibitors; quinaprilate, cilazapril, moexipril, trandolapril, spirapril, imidapril; angiotensin II antagonists; candesartancilexetil, valsartan, telmisartan, olmesartanmedoxomil, eprosartan; peripherally active alpha-receptor blockers such as prozosin, urapidil, doxazosin, bunazosin, terazosin, indoramin, atc.; vaspdilatator such as dihydralazine, diisopropylamine dichloraetate, minoxidil, sodium nitroprusside, etc.; other anti-hypertensive agents such as indapamide, co-dergocrine mesylate, dihydroergotoxin methanesulfonate, cicletanin, bosetan, fludrocortisones, etc.; phosphodiesterase inhibitors such as milrinon, enoximon and, in particular, antihypertenstive agents such as adrenergic and dopaminergic substances, for example, dobutamine, ephinephrine, etilefrine, norfenefrine, norepinephrine, oxilofrine, dopamine, midodrine, pholedrine, ameziniummetil, etc.; partial adrenoceptor agonists such as dihydroergotamine; inflammatory cytokines such as fibronectin, polylysine, ethylene vinyl acetate, TGFβ, PDGF, VEGF, bFGF, TNFa, NGF, GM-CSF, IGF-a, IL-1, IL-8, IL-6, growth hormone, etc.; adhesive substances such as cyanoacrylate, beryllium, silica, etc.; growth factors such as erythromycin, hormones such as corticotrophin, gonadotropin, somatropin, thyrotrophin, desmopressin, terlipressin, pxytocin, cetrorelix, corticorelin, leuprorelin, triptorelin, gonadorelin, ganirelix, buserelin, nafarelin, goserelin, etc., and regulator peptides such as somatostatin, octreotid, etc.; bone and cartilage stimulating peptide, recombinant human BMP-2 (rhBMP-2), recombinant BMPs such as bisphophonate (e.g., riseddronate, pamidronate, ibandronate, zoledronic acid, clodronic acid, etidronic acid, alendronic acid, tiludronic acid), bone morphogenetic proteins (BMPs) including fluorides such as disodium fluorophosphates, sodium fluoride, etc.; calcitonin, dihydrotachystyrol; epidermal growth factor (EGF), platelet-derived growth factor (PDGF), fibroblast growth factor (FGFs), transforming growth factor-b (TGFs-b), transforming growth factors-a (TGFs-a), erythropoietin (EPO), insuline-like growth factor-I (IGF-I), insuline-like growth factor-II (IGF-II), interleukin-1 (IL-1), interleukin-2 (IL-2), interleukin-6 (IL-6), interleukin-8 (IL-8), tumor necrosis factor-a (TNF-a), tumor necrosis factor-b (TNF-b), interferon-g (INF-g), colony stimulating factors (CSFs); monocyte chemotactic protein, fibroblast stimulating factor 1, histamine, fibrin or fibrinogen, endothelin-1, angiotensin II, collagen, bromocriptine, methysergide, methotrexate, carbon tetrachloride, thioacetamide and ethanol; further, silver (ions), titanium dioxide, in particular, for example, β-lactamase-sensitive penicillin such as benzyl penicillin (penicillin G), phenoxymethylpenicillin (penicillin V); for example, β-lactamase-resistant penicillin such as amoxicillin, ampicillin, bacampicillin, etc.; acylamino penicillin such as mezlocillin, piperacillin, etc.; carboxyl penicillin such as cefazoline, cefuroxim, cefoxitin, cefotiam, cefaclor, cefadroxil, cefalexin, loracarbef, cefixim, cefuroximaxetil, ceftibuten, cefpodoximproxetil, etc.; aztreonam, ertapenem, meropenem; β-lactam inhibitors such as sulbactam, sultamicillintosylate, etc.; tetracycline such as doxycycline, minocycline, tetracycline, chlorotetracycline, oxytetracycline, etc ; aminoglycosides such as gentamicin, neomycin, streptomycin, tobramycin, amikacin, netilmicin, paromomycin, framyceetin, spectinomycin, etc.; macrolide antibiotics such as azithromycin, clarithromycin, erythromycin, roxithromycin, spiramycin, josamycin, etc.; lincosamide such as clindamycin, lincomycin, etc.; gyrase inhibitors such as fluoroquinolones, for example, ciprofloxacin, ofloxacin, moxifloxacin, norfloxacin, gatifloxacin, enoxacin, fleroxacin, levofloxacin, etc.; quinolones such as pipemidic acid; sulfonamide, trimethoprim, sulfadiazine, sulfalene; glycopeptides antibiotics such as vancomycin, teicoplanin, etc.; polypeptide antibiotics such as colistin, polymyxin, for example, polymyxin-b, etc., nitroimidazole derivatives, for example, metronidazole, tinidazole, etc.; aminoquinolone such as cloroquin, mefloquin, hydroxychloroquin, etc.; biguanid such as proguanil; quinine alkaloids such as pyrimethamine, and diaminopyrimidine; amphenicol such as chloramphenicol; rifabutin, dapson, fusidic acid, fosfomycin, nifuratel, telithromycin, fusafungin, pentamidine diisethionate, rifampicin, taurolidin, atovaquon, linezolid, etc.; virus statics such as aciclovir, ganciclovir, famciclovir, foscarnet, ionsine-(dimepranol-4-acetanidobenzoate), valganciclovir, valaciclovir, cidofovir, brivudin, etc.; antiretroviral active ingredient nucleoside analog reverse-transcriptase inhibitors and derivatives such as lamivudine, zalcitabine, didanosine, zidovudin, tenofovir, stavudin, avacavir, etc.; non-nucleoside analog reverse-transcriptase inhibitor; amprenavir, indinavir, saquinavir, lopinavir, ritonavir, nelfinavir; amantadine, ribavirin, zanamivir, oseltamivir, lamivudine, and any combination thereof and mixtures thereof.

The therapeutically active agent may include, for example, anti-depressants, anti-psychotics or anti-anxiety agents, such as alprazolam, amoxapine, bentazepam, bromazepam, chlorazepine, chlobazam, clotiazepam, diazepam, lorazepam, flunitrazepam, flurazepam, lormetazepam, medazepam, nitrazepam, oxazepam, temazepam, maprotilline, mianserin, notriptyline, risperidone, sertraline, trazodone, baloperidol, trimipramine maleate fluoxetine, ondansetron, midazolam, chlorpromazine, haloperidol, triazolam, clozapine, fluorpromazine, fluphenazine decanoate, fluanisone, perphenazine, pimozide, prochlorperazine, sulfiride, thioridazine, paroxetine, citalopram, bupropion, phenelzine, olanzapine, divalprox sodium and venlafaxine.

The therapeutically active agent may include, for example, opioid receptor agonists and antiagonists, a compound that exhibits agonist/antagonist combined activity, and a compound that exhibits partial activity, such as morphine, depot morphine, etorphine, diacetyl morphine, hydromorphine, oxymorphone, levorphanol, methadone, levomethadyl, meperidine, fentanyl, sufentanil, alfentail, codeine, hydrocodone, oxycodone, tevine, desomorphine, nicomorphine, dipropanoyl morphine, benzyl morphine, ethyl morphine, pethidine, tramadol, dextropropoxyphene; naloxone and naltrexone; buprenorphine, nalbuphine, butorphanol, pentazocine and ethyl ketocyclazocine.

The therapeutically active agent may include, for example, tricyclic compounds, such as azothiophene, amitriphthyline, famotidine, promethazine, paroxatine, oxycarbazepine and mirtazapine.

The therapeutically active agent may include, for example, antidiabetic drugs, such as acetohexamide, chlorpropamide, glibenclamide, gliclazide, glipizide, metformine, tolazamide, glyburide, glimepiride and tolbutamide.

The therapeutically active agent may include, for example, anti-epileptic agents, such as beclamide, carbamazepine, gabapentine, tiagabine, vigabatrin, topiramate, clonazepam, ethotoin, methoin, methsuximide, methyl phenovabiton, oxycarbazepin, paramethadione, phenacemide, phenovabiton, phenyloin, phensuximide, primidone, sultiamine, sodium phenytoin, nitrofurantoin monohydrate, gabapentin, lamotrigine, zonisamide, ethosuximide and valproic acid.

The therapeutically active agent may include, for example, hypnotic/sedative drugs and/or muscle relaxants, such as zolpidem tartrate, amylobabitone, babitone, butobabitone, pentobabitone, brotizolam, carbromal, chlordiazepoxide, chlormethiazole, ethinamate, meprobamate, metacualom, cyclobenzaprene, cyclobenzaprine, tizanidine, baclifen, butalbital, zopiclone, atracurium, tubocurarine and phenobarbital.

The therapeutically active agent may include, for example, antifungals, antiprotozoals or antiparasitics, such as: amphotericin, butoconazole nitrate, clotrimazole, econazole nitrate, fluconazole, flucytosine, glyceofluvin, itraconazole, ketoconazole, miconazole, natamycin, nystatin, sulconazole nitrate, terconazole, tioconazole and udecenoic acid; benznidazole, clioquinol, decoquinate, diiodo hydroxyquinoline, diloxanide furoate, dinitolmide, furazolidone, metronidazole, nimorazole, nitrofurazone, ornidazole, terbinafine, clotrimazole, chloroquine, mefloquine, pyrimethamine, praziquantel, quinacrine, mebendazole and tinidazole.

The therapeutically active agent may include, for example, anti-hypertensive agents or cardiologic drugs, such as candesartan, hydralazine, clonidine, triamterene, felodipine, gemfibrozil, fenofibrate, nifedical, prazosin, mecamylamine, doxazosin, dobutamine and cilexetil.

The therapeutically active agent may include, for example, anti-migraine drugs, such as dihydroergotamine mesylate, ergotamine tartrate, methysergide maleate, pizotifen maleate and sumatriptan succinate.

The therapeutically active agent may include, for example, anti-muscarinic agents, such as atropine, benzhexol, biperiden, ethopropazine, hyoscyamine, mepenzolate bromide, oxybutynin, oxypencyclimine and tropicamide.

The therapeutically active agent may include, for example, anti-neoplastic agents (or immune suppressants), such as aminoglutethimide, amsacrin, azathioprine, busulfan, chlorambucil, cyclosporine, dacarbazine, estramustine, etoposide, lomustine, melphalan, mercaptopurine, methoclexate, mitomycin, mitotan, mitoxanthrone, procarbazine, tamoxifen citrate, testolactone, tacrolimus, mercaptopurine and sirolimus.

The therapeutically active agent may include, for example, anti-Parkinson's agents, such as bromocriptine mesylate, levodopa, tolcapone, ropinirole, bromocriptine, hypoglycemic agents, for example, sulfonylurea biguanide, alpha-glucosidase inhibitor, thiazolidinedione, cabergoline, carbidopa and lisuride maleate.

The therapeutically active agent may include, for example, anti-thyroid agents such as carbimazole and propythiouracil.

The therapeutically active agent may include, for example, inotropics, such as amrinone, milrinone, digitoxin, enoximone, lanatoside C and medigoxin.

The therapeutically active agent may include, for example, hypolipidemia or hyperlipidemia drugs such as fenofibrate, clofibrate, probucol, ezetimibe and torcetrapib, etc.

The therapeutically active agent may include, for example, anti-inflammatory agents such as meloxicam, triamcenolone, cromolyn, nedocromil, hydroxychloroquine, montelukast, zileuton, and zafirlukast.

The therapeutically active agent may include, for example, anti-histamine drugs such as fexofenadine, chloral hydrate, hydroxyzine, promethazine, cetirizine, cimetidine, cyclizine, meclizine, dimenhydrinate, loratadine, and nizatidine.

The therapeutically active agent may include, for example, antiulcer drugs such as omeprazole, lansoprazole, pantoprazole and ranitidine.

The therapeutically active agent may include, for example, diuretics such as hydrochlorothiazide, amyloride, acetazolamide, furosemide and torsemide.

The therapeutically active agent may include retinoids, for example: first generation retinoids such as retinol, retinal, tretinoin (retinoic acid, retin-A), isotretinoin and alitretinoin; second generation retinoids such as etretinate and acitretin as a metabolite thereof; and third generation retinoids such as tazarotene, bexarotene and adapalene.

The therapeutically active agent may include, for example, statin and derivatives thereof, such as atorvastatin, fluvastatin, lovastatin, nystatin, rosuvastatin, pravastatin, orlistat and simvastatin.

The therapeutically active agent may include, for example, stimulants such as amphetamine, phentermine, tyramine, ephedrine, metaraminol, phenylephrine, dexamphetamine, dexfenfluramine, fenfluramine, nicotine, caffeine and mazindol.

The therapeutically active agent may include, for example, vasodilators such as carvedilol, terazosine, phentolamine and menthol The therapeutically active agent may include, for example, anti-Alzheimer drugs such as levetiracetam, levitiracetam and donepezil.

The therapeutically active agent may include, for example, ACE inhibitors such as benzapril, enalapril, ramipril, fosinopril sodium, lisinopril, minoxidil, isosorbide, ramipril and quinapril.

The therapeutically active agent may include, for example, beta-adrenaline receptor antagonists such as atenolol, timolol, pindolol, pronanolol hydrochloride, bisoprolol, esmolol, metoprolol succinate, metoprolol and metoprolol tartrate.

The therapeutically active agent may include, for example, angiotensin II antagonists such as losartan.

The therapeutically active agent may include, for example, platelet inhibitors such as abciximab, clopidogrel, tirofiban and aspirin.

The therapeutically active agent may include, for example, alcohols or phenols, such as tramadol, tramadol hydrochloride, allopurinol, calcitriol, cilostazol, sotalol, urasodiol bromperidol, droperidol, flupentixol decanoate, albuterol, albuterol sulfate, carisoprodol, clobetasol, ropinirole, labetalol and methocarbamol.

The therapeutically active agent may include, for example, ketones or esters such as amiodarone, fluticasone, spirolactone, prednisone, triazodone, desoxymetasone, methyl prednisone, benzonatate nabumetone and buspirone.

The therapeutically active agent may include, for example, anti-vomiting drugs such as metoclopramide.

The therapeutically active agent may include, for example, ophthalmologic treatment drugs such as dorzolamide, brimonidine, olopatadine, cyclopentolate, pilocarpine and ecothiopate.

The therapeutically active agent may include, for example, anti-coagulant agents or anti-thrombotic agents such as warfarin, enoxaparin and lepirudin.

The therapeutically active agent may include, for example, gout treatment drugs such as probenecid and sulfin pyrazone.

The therapeutically active agent may include, for example, COPD or asthma treatment drugs such as ipratropium.

The therapeutically active agent may include, for example, osteoporosis treatment drugs such as raloxifene, pamidronate and risedronate.

The therapeutically active agent may include, for example, peptides for cosmetics, such as acetyl hexapeptide-3, acetyl hexapeptide-8, acetyl octapeptide and 1-carnosine.

The therapeutically active agent may include, for example: vaccine including toxoid (inactivated toxic compound); protein, protein subunit and polypeptide; polynucleotide such as DNA and RNA; conjugates; vaccine including saponin, virosome, inorganic and organic adjuvants, for example, zostavax.

The therapeutically active agent may include nutritional medical or cosmetic medical active substances, including, for example: Q10 (or ubiquione), ubiquinol or lesveratrol; carotenoids such as α, β or γ-carotene, lycopene, lutein, zeaxanthin and astaxanthin; plant nutrients such as lycopene, lutein, and thiaxanthin; omega-3-fatty acids including linoleic acid, conjugated linoleic acid, docosahexaenoic acid (DHA), eicosapentaenoic acid (EPA) and their glycerolesters; oil-soluble vitamins including vitamin D (D2, D3 and derivatives thereof), vitamin E (α, β, γ, δ-tocopherol or α, β, γ, δ-tocotrienol), vitamin A (retinol, retinal, retinoic acid and derivatives thereof), vitamin K (K1, K2, K3, and derivatives thereof), capric/caprylic triglycerides, folic acid, iron, niacin, glyceryl linoleate, omega-6 fatty acids, vitamin F, selenium, cyanocobalamin, aloe vera, beta-glucan, bisabolol, Camellia Tea (green tea) extract, capric/caprylic triglyceride, centella asiatica (gotu cola) extract, cetearyl olivate, chlorophyll, orange oil, cocoyl proline, dicaprylyl ether, disodium lauriminodipropionate tocopheryl phosphate (vitamin E phosphate), glycerin, glyceryl oleate, licorice extract, hazel (witch hazel) extract, lactic acid, lecithin, lutein, macadamia seed oil, chamomile extract, evening primrose oil, olive leaf extract, rice bran oil, avocado oil, Polygonum Multiflorum root extract, pomegranate sterols, resveratrol, rose oil, sandalwood oil, titanium dioxide, vitamins A palmitate, grape seed oil, halobetasol, adenosine, adenosine triphosphate, alpha hydroxyl acid, allantoin, hyaluronic acid and derivatives, isolutrol, tranexamic acid, glycolic acid, arginine, ascorbyl glucosamine, ascorbyl palmitate, salicylic acid, carnosic acid, alpha-lipoic acid, gamma-linolenic acid (GLA), panthenol, retinyl propionate, retinyl palmitate, furfuryl adenine, retin aldehyde, glypeptide, idebenone, dimethylaminoethanol (DMAE), niacinamide, beta-glucan, palmitoyl pentapeptide-4, palmitoyl oligopeptide/tetrapeptide-7, etoshine, ceramide, phenylalanine, glucuronolactone, L-carnitine, hydroxyapatite, palmitoyl tripeptide-3, phoscholine, zinc oxide, a-bisabolol, eugenol, silibinin, soy isoflavones, catalpol, Arnica chamissonis-derived pseudoguaianolide, rosmarinic acid, rosmanol, salicylate, for example, salicin, saligenin and salicylic acid, taraxasterol, α-lactucerol, iso-lactucerol, taraxacoside, ceremide, arbutin, gingerol, shogaol, hypericin, elastin, collagen and peptides thereof.

Porous Silica Particles

Silica particles according to the present invention (porous silica particle, pSP) are particles of silica material ($SiO_2$) having a nano-sized particle diameter.

Silica nanoparticles according to the present invention are porous particles having nano-sized pores.

The porous silica particles according to the present invention may support a bioactive substance on an outer surface of the particle or inside the pore.

The porous silica particle according to the present invention is biodegradable and may support the bioactive substance in vivo and, when administered into the body, be biodegraded to release the bioactive substance.

That is, the porous silica particles are biodegraded to release the bioactive substance. In particular, the porous silica particles according to the present invention are gradually degradable in vivo, enabling the supported bioactive substance to have sustained-releasing properties. For example, 't' at which a ratio of absorbance in the following Equation 1 reaches ½ is 24 or more.

$$A_t/A_0 \qquad \text{[Equation 1]}$$

wherein, $A_0$ denotes an absorbance of porous silica particles measured after putting 5 ml of a suspension including 1 mg/ml of the porous silica particles in a cylindrical permeable membrane having pores with a diameter of 50 kDa, wherein 15 ml of a solvent in contact with the permeable membrane and substantially identical to the suspension is present outside the permeable membrane, inner and outer portions of the permeable membrane are horizontally agitated at 37° C. and 60 rpm, the suspension has pH 7.4, and wherein $A_t$ denotes an absorbance of the porous silica particles measured 't' hour after the measurement of $A_0$.

Equation 1 indicates a rate at which the porous silica particles are degraded in an environment similar to in vivo physiological conditions.

Figure 7:
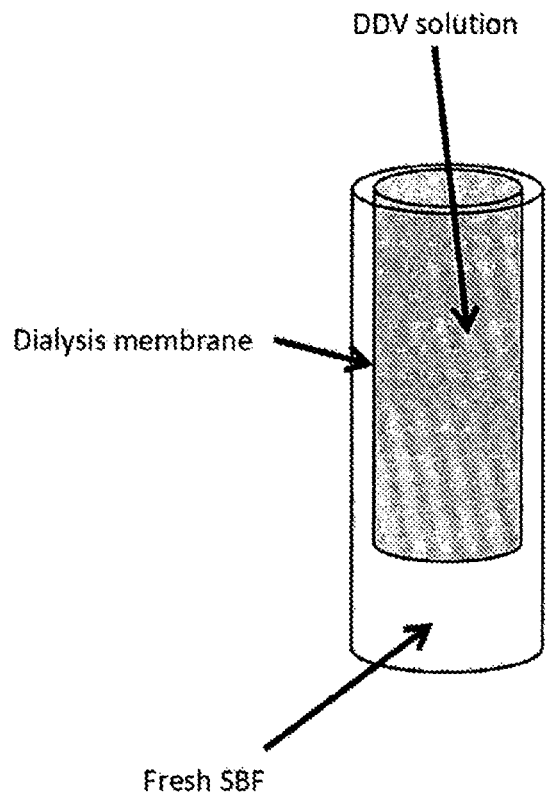
FIG. 7 illustrates a tube provided with a cylindrical permeable membrane according to one example

The absorbance $A_0$, and $A_t$ in Equation 1 may be determined, as illustrated in FIG. 7, by putting the porous silica particles and the suspension in the cylindrical permeable membrane and also pouring the same suspension outside the permeable membrane, and then, measuring the absorbance.

The porous silica particles of the present invention may be biodegradable and slowly degraded in the suspension. Since a diameter of 50 kDa approximately corresponds to 5 nm, the biodegraded porous silica particles may pass through the permeable membrane with the diameter of 50 kDa. The cylindrical permeable membrane is under horizontal agitation at 60 rpm so as to be homogeneously mixed while the degraded porous silica particles may optionally come out through the permeable membrane.

The absorbance in Equation 1 may be determined in an environment, for example, in which the suspension outside the permeable membrane is replaced with a new suspension. The suspension may be continuously changed or replaced at a predetermined time period. Herein, the predetermined time period may be a regular or irregular period of time. For example, the suspension may be replaced at a predetermined interval in a range of 1 hour to 1 week, every hour, every 2 hours, every 3 hours, every 6 hours, every 12 hours, every 24 hours, every 2 days, 3 days, 4 days, 7 days, etc., but it is not limited thereto.

The ratio of absorbance reaching ½ means that the absorbance after the time 't' becomes half of the initial absorbance, and thus indicating that approximately half of the porous silica particles have been degraded.

The suspension may be a buffer solution and, specifically, at least one or more selected from the group consisting of phosphate buffered saline (PBS) and simulated body fluid (SBF), and more specifically, PBS.

According to the present invention, 't' at which the ratio of absorbance determined by Equation 1 reaches ½, may be 24 or more, for example, 't' may range from 24 to 120, and more specifically, 24 to 96, 24 to 72, 30 to 70, 40 to 70, 50 to 65, etc. within the above range, but it is not limited thereto.

With regard to the porous silica particles according to the present invention, 't' at which the ratio of absorbance determined by Equation 1 reaches ⅕, for example, may range from 70 to 140, and more specifically, 80 to 140, 80 to 120, 80 to 110, 70 to 140, 70 to 120, 70 to 110, etc. within the above range, but it is not limited thereto.

With regard to the porous silica particles according to the present invention, 't' at which the ratio of absorbance determined by Equation 1 reaches 1/20, for example, may range from 130 to 220, and more specifically, 130 to 200, 140 to 200, 140 to 180, 150 to 180, etc. within the above range, but it is not limited thereto.

Further, with regard to the porous silica particles according to the present invention, 't' at which the ratio of absorbance determined by Equation 1 becomes 0.01 or less, for example, may be 250 or more, and more specifically, 300 or more, 350 or more, 400 or more, 500 or more, 1000 or more, etc., and may further have an upper limit of 2000, but it is not limited thereto.

With regard to the porous silica particles according to the present invention, the ratio of absorbance determined by Equation 1 and 't' have a high level positive correlation. For example, Pearson's correlation coefficient may be 0.8 or more, for example, 0.9 or more, and 0.95 or more.

't' in Equation 1 indicates the rate at which the porous silica particles are degraded in the environment similar to in vivo physiological conditions, and may be controlled by adjusting, for example, a surface area, particle diameter and pore diameter of the porous silica particle, substitutes on the surface of the particle and/or inside the pore, compactness of the surface or the like.

For example, it is possible to reduce t by increasing the surface area of the particle or to increase t by decreasing the same. The surface area may controlled by adjusting the diameter of the particle, or the diameter of the pore. Further, placing a substituent on the surface of the particle and/or inside the pore may reduce direct exposure of the porous silica particles to environments (solvent, etc.), thereby increasing t. Further, direct exposure of the porous silica particles to the environments may be reduced by supporting the bioactive substance on the porous silica particles and increasing affinity between the bioactive substance and the porous silica particles, thereby increasing 't'. Further, 't' may be increased by more densely forming the surface of the particle during preparation of the particles. Hereinabove, various examples of controlling 't' in Equation 1 have been described, but it is not limited thereto.

The porous silica particle according to the present invention may be a spherical particle, but it is not limited thereto.

The porous silica particle according to the present invention may have a mean diameter of, for example, 150 nm to 1000 nm, and more specifically, 150 nm to 800 nm, 150 nm to 500 nm, 150 nm to 400 nm, 150 nm to 300 nm or 150 nm to 200 nm within the above range, but it is not limited thereto.

The porous silica particle according to the present invention may have a mean pore diameter of, for example, 1 nm to 100 nm, and more specifically, 5 nm to 100 nm, 7 nm to 100 nm, 7 nm to 50 nm, 10 nm to 50 nm, 10 nm to 30 nm or 7 nm to 30 nm within the above range, but it is not limited thereto. If having the large diameter as described above, a large amount of bioactive substances may be supported and even the bioactive substances having a large size may also be supported.

The porous silica particle according to the present invention may have a BET surface area of, for example, 200 m$^2$/g to 700 m$^2$/g. For example, the BET surface area may range from 200 m$^2$/g to 700 m$^2$/g, 200 m$^2$/g to 650 m$^2$/g, 250 m$^2$/g to 650 m$^2$/g, 300 m$^2$/g to 700 m$^2$/g, 300 m$^2$/g to 650 m$^2$/g, 300 m$^2$/g to 600 m$^2$/g, 300 m$^2$/g to 550 m$^2$/g, 300 m$^2$/g to 500 m$^2$/g, 300 m$^2$/g to 450 m$^2$/g, or the like, within the above range, but it is not limited thereto.

The porous silica particle according to the present invention may have a volume per g (volume/g) of, for example, 0.7 ml to 2.2 ml. For example, the volume/g may range from 0.7 ml to 2.0 ml, 0.8 ml to 2.2 ml, 0.8 ml to 2.0 ml, 0.9 ml to 2.0 ml, 1.0 ml to 2.0 ml within the above range, but it is not limited thereto. If the volume/g is excessively small, the degradation rate is too high. Further, excessively large particles are hardly prepared or do not have a complete shape.

The porous silica particle according to the present invention may have a hydrophilic substituent and/or a hydrophobic substituent on the outer surface of the particle and/or inside the pore. For example, hydrophilic substituent only or hydrophobic substituent only may be present in both the surface and the inside the pore. Otherwise, the hydrophilic substituent or hydrophobic substituent may be present in either the surface of the particle or the inside the pore. Alternatively, the hydrophilic substituent may be present on the surface of the particle while the hydrophobic substituent may be present inside the pore, and vice versa.

The bioactive substance is generally released by degradation of nanoparticles. Therefore, interaction of the porous silica particles to a bioactive substance release environment may be controlled by adjusting the substituent, which in turn may adjust a degradation rate of nanoparticle itself, thereby controlling a release rate of the bioactive substance. Further, the bioactive substance may be diffused and released from the nanoparticles, wherein a binding force of the bioactive substance to nanoparticles may be regulated by adjusting the substituent, thereby controlling the release of the bioactive substance.

Further, in order to improve the binding force to a non-soluble (hydrophobic) bioactive substance, some operations may be performed such that a hydrophobic substituent is present inside the pore while affording a hydrophilic substituent on the surface of the particle, in consideration of ease of use and formulation.

The hydrophilic substituent may include, for example, hydroxy, carboxy, amino, carbonyl, sulfhydryl, phosphate, thiol, ammonium, ester, imide, thioimide, keto, ether, indene, sulfonyl, or polyethyleneglycol group, etc. Further, the hydrophobic substituent may include, for example, substituted or unsubstituted C1 to C30 alkyl, substituted or unsubstituted C3 to C30 cycloalkyl, substituted or unsubstituted C6 to C30 aryl, substituted or unsubstituted C2 to C30 heteroaryl, halogen, C1 to C30 ester, halogen-containing group, etc.

Further, the porous silica particle according to the present invention may be positively or negatively charged on the outer surface of the particle and/or inside the pore. For example, both the outer surface of the particle and the inside the pore may be positively or negatively charged. Further, either the outer surface of the particle or the inside the pore may be positively or negatively charged. Otherwise, the outer surface of the particle may be positively charged whereas the inside the pore may be negatively charged, and vice versa.

The charging may be performed by the presence of cationic substituents or anionic substituents.

The cationic substituent may include, for example, a basic group such as amino or a nitrogen-containing group, while the anionic substituent may include, for example, an acidic group such as carboxyl (—COOH), sulfonic acid (—SO$_3$H), thiol (—SH), etc., but it is not limited thereto.

Similarly, the interaction of the porous silica particles to the bioactive substance release environment may be controlled by the charging, which in turn may adjust a degradation rate of nanoparticles, thereby controlling a release rate of the bioactive substance. Alternatively, the bioactive substance may be diffused and released from the nanoparticles, and when adjusting the substituent, the binding force of the bioactive substance to the nanoparticles may be adjusted, thereby controlling release of the bioactive substance.

Further, the porous silica particle according to the present invention may contain a substituent, which is used for supporting the bioactive substance on the surface of the particle and/or inside the pore, delivering the bioactive substance to target cells, supporting a material useful for other purposes, or bonding other additional substituent, in addition to the aforementioned objects. In addition, the porous silica particle may further include an antibody, ligand, cell-permeable peptide or aptamer bound to the substituent.

The substituent, charge, binding material, etc. described above may be added, for example, by surface modification.

The surface modification may be performed, for example, by reacting a compound containing a substituent to be introduced with particles, wherein the compound may be, for example, alkoxysilane having C1 to C10 alkoxy group, but it is not limited thereto. The alkoxysilane has one or more of the alkoxy group, for example, 1 to 3 alkoxy groups. Alternatively, the alkoxysilane may include a substituent to be introduced at a site to which the alkoxy group is not bonded, or another substituent substituted by the above substituted.

Preparation of Porous Silica Particles

The porous silica particles according to the present invention may be formed by, for example, processes for preparation of particles having small pores and expansion of the pores. If necessary, the particles may be formed through further processes of calcination, surface modification and the like. When both processes of the calcination and the surface modification have been conducted, the particles may be surface-modified after the calcination.

The particle having small pores may have an average pore diameter of, for example, 1 to 5 nm.

The particle having small pores may be obtained by adding a surfactant and a silica precursor to a solvent, followed by agitation and homogenization.

The solvent used herein may be water and/or an organic solvent. The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane or the like. Preferably, alcohol and, more preferably, methanol may be used, but it is not limited thereto.

When using a mixed solvent of water and the organic solvent, a relative ratio therebetween may be in a ratio by volume of 1:0.7 to 1.5, for example, 1:0.8 to 1.3, but it is not limited thereto.

The surfactant may include, for example, cetyltrimethylammonium bromide (CTAB), hexadecyltrimethylammonium bromide (TMABr), hexadecyltrimethylpyridinium chloride (TMPrCl), tetramethylammonium chloride (TMACl) or the like. Preferably, CTAB is used.

The surfactant may be added in an amount of 1 to 10 g to 1 liter of the solvent, for example, 1 to 8 g, 2 to 8 g, 3 to 8 g, or the like within the above range, but it is not limited thereto.

The silica precursor may be added after adding the surfactant to the solvent and agitating the same. The silica precursor may include, for example, tetramethyl orthosilicate (TMOS), but it is not limited thereto.

For instance, the agitation may be conducted for 10 to 30 minutes, but it is not limited thereto.

The silica precursor may be added in an amount of 0.5 to 5 ml to 1 liter of the solvent, for example, 0.5 to 4 ml, 0.5 to 3 ml, 0.5 to 2 ml, 1 to 2 ml, or the like within the above range, but it is not limited thereto.

If necessary, sodium hydroxide may be further added as a catalyst. In this case, this compound may be added while agitating the same after adding the surfactant and before adding the silica precursor to the solvent.

The sodium hydroxide may be added in an amount of 0.5 to 8 ml to 1 liter of the solvent in terms of 1 M sodium hydroxide solution, for example, 0.5 to 5 ml, 0.5 to 4 ml, 1 to 4 ml, 1 to 3 ml, 2 to 3 ml, or the like within the above range, but it is not limited thereto.

After adding the silica precursor, the solution may undergo a reaction under agitation. The agitation may be conducted for 2 to 15 hours, for example, 3 to 15 hours, 4 to 15 hours, 4 to 13 hours, 5 to 12 hours, 6 to 12 hours, 6 to 10 hours, or the like within the above range, but it is not limited thereto. If the agitation time (reaction time) is too short, it may result in insufficient nucleation.

After the agitation, the solution may be subjected to aging. The aging may be conducted for 8 to 24 hours, for example, 8 to 20 hours, 8 to 18 hours, 8 to 16 hours, 8 to 14 hours, 10 to 16 hours, 10 to 14 hours, or the like within the above range, but it is not limited thereto.

Thereafter, a reaction product may be washed and dried to prepare porous silica particles.

If necessary, unreacted materials may be removed before washing.

For instance, such removal may be conducted by separating a supernatant through centrifugation.

The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

The washing may be conducted with water and/or an organic solvent. More particularly, since different types of materials are dissolved in different solvents, water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane or the like. Preferably, alcohol and, more preferably, ethanol may be used, but it is not limited thereto.

The washing may be conducted under centrifugation, for example, at 6,000 to 10,000 rpm. The washing may be conducted for 3 to 60 minutes, for 3 to 30 minutes, 4 to 30 minutes, 5 to 30 minutes, or the like within the above range, but it is not limited thereto.

Alternatively, the washing may be conducted while filtering the particles through a filter without centrifugation. The filter used herein may be provided with pores having a pore diameter equal to or less than the diameter of the porous silica particles. By filtering the reacting solution, the particles only remain on the filter, and may be washed by pouring water and/or an organic solvent onto the filter.

During washing, the water and organic solvent may be used once or several times by turns. Otherwise, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at, for example, 20° C. to 100° C., but it is not limited thereto. Alternatively, the drying may be conducted under a vacuum condition.

Thereafter, the obtained porous silica particles may undergo pore expansion.

The pore expansion may be conducted using a pore expanding agent.

The pore expanding agent used herein may include, for example, trimethylbenzene, triethylbenzene, tripropylbenzene, tributylbenzene, tripentylbenzene, trihexylbenzene, toluene, benzene or the like. Preferably, trimethylbenzene may be used, but it is not limited thereto.

Further, the pore expanding agent used herein may include, for example, N,N-dimethylhexadecylamine (DMHA), but it is not limited thereto.

The pore expansion may be conducted by, for example, mixing the porous silica particles in a solvent with the pore expanding agent and heating the same to conduct a reaction.

The solvent used herein may include water and/or an organic solvent. The organic solvent may include, for example ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc. Preferably, alcohol and, more preferably, ethanol may be used, but it is not limited thereto.

The porous silica particles may be added in an amount of 10 to 200 g to 1 liter of the solvent, for example, 10 to 150 g, 10 to 100 g, 30 to 100 g, 40 to 100 g, 50 to 100 g, 50 to 80 g, 60 to 80 g, or the like within the above range, but it is not limited thereto.

The porous silica particles may be uniformly dispersed in the solvent. For instance, the porous silica particles may be added to the solvent, followed by ultrasonic dispersion. When using a mixed solvent, the porous silica particles may be dispersed in a first solvent, followed by adding the same to a second solvent.

The pore expanding agent may be added in an amount of 10 to 200 parts by volume ('vol. parts') to 100 vol. parts of the solvent, for example, 10 to 150 vol. parts, 10 to 100 vol. parts, 10 to 80 vol. parts, 30 to 80 vol. parts, 30 to 70 vol. parts, or the like within the above range, but it is not limited thereto.

The reaction may be conducted at 120 to 180° C., for example, at 120 to 170° C., 120 to 160° C., 120 to 150° C., 130 to 180° C., 130 to 170° C., 130 to 160° C., 130 to 150° C., or the like within the above range, but it is not limited thereto.

The reaction may be conducted for 24 to 96 hours, for example, 30 to 96 hours, 30 to 96 hours, 30 to 90 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, or the like within the above range, but it is not limited thereto.

By adjusting the time and the temperature within the above-exemplified ranges, the reaction may be sufficiently but not excessively conducted. For instance, as the reaction temperature is decreased, the reaction may be conducted with increased reaction time. On the other hand, when the reaction temperature is decreased, the reaction time may be decreased. If the reaction is insufficiently performed, pore expansion may also be not sufficient. On the other hand, if the reaction is redundantly performed, particles may be collapsed due to over-expansion of pores.

The reaction may be conducted, for example, while raising a reaction temperature stepwise. More particularly, the reaction may be conducted by raising the temperature stepwise from room temperature to the above temperature at a rate of 0.5° C./min to 15° C./min, for example, 1° C./min to 15° C./min, 3° C./min to 15° C./min, 3° C./min to 12° C./min, 3° C./min to 10° C./min, or the like within the above range, but it is not limited thereto.

After the reaction, the reacting solution may be gradually cooled, for example, the temperature may be decreased stepwise to cool the reacting solution. In particular, the cooling may be conducted by decreasing the above temperature to room temperature stepwise at a rate of 0.5° C./min to 20° C./min, for example, 1° C./min to 20° C./min, 3° C./min to 20° C./min, 3° C./min to 12° C./min, 3° C./min to 10° C./min, or the like within the above range, but it is not limited thereto.

After the cooling, the reaction product may undergo washing and drying to prepare porous silica particles having expanded pores.

If necessary, unreacted materials may be removed before washing.

For instance, such removal may be conducted by separating a supernatant through centrifugation.

The centrifugation may be conducted at 6,000 to 10,000 rpm. Further, the centrifugation may be conducted for 3 to 60 minutes, for example, 3 to 30 minutes, 4 to 30 minutes, 5 to 30 minutes, or the like within the above range, but it is not limited thereto.

The washing may be conducted using water and/or an organic solvent. More particularly, since different types of materials are dissolved in different solvents, water and the organic solvent may be used once or several times by turns. Alternatively, the water or organic solvent may be used alone for washing once or several times. The several times may range from 2 to 10 times, for example, 3 times, 4 times, 5 times, 6 times, 7 times, 8 times or the like.

The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc. Preferably, alcohol and, more preferably, ethanol may be used, but it is not limited thereto.

The washing may be conducted under centrifugation at 6,000 to 10,000 rpm. Further, the centrifugation may be conducted for 3 to 60 minutes, for example, 3 to 30 minutes, 4 to 30 minutes, 5 to 30 minutes, or the like within the above range, but it is not limited thereto.

The washing may also be conducted by filtering the particles without centrifugation. The filter may have a pore diameter equal to or less than the diameter of the porous silica particles. The particles only may remain on the filter by filtering the reacting solution and be washed by pouring water and/or an organic solvent into the filter.

The water and organic solvent may be used once or several times by turns during washing. Otherwise, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at 20 to 100° C., but it is not limited thereto. Further, the drying may also be conducted under a vacuum condition.

Thereafter, the obtained particles may undergo calcination.

The calcination is a process of heating particles to endow the surface and inside of the particle with a more compact structure while removing any organic matter filled in the pores of the particles.

Thereafter, the obtained particles may undergo surface modification.

The surface modification may be conducted on the surface and/or inside the pore. The surface of the particle and the inside the pores of the particle may be modified in the same manner as or different manners from each other.

The modification can allow the particles to be charged or have hydrophilicity and/or hydrophobicity. The modification may be conducted by reacting a compound having hydrophilic, hydrophobic, cationic or anionic substituents, which are intended to be introduced, with the particles, but it is not limited thereto. The above compound may be, for example, alkoxysilane having C1 to C10 alkoxy group, but it is not limited thereto. The alkoxylsilane may have at least one alkoxyl group, for example, 1 to 3 alkoxy groups and may have a substituent intended to be introduced or another substituent substituted with the above substituent at a site to which the alkoxy group is not bonded.

Reacting the alkoxysilane with the porous silica particles may form a covalent bond between a silicon atom and an oxygen atom, thus to allow the alkoxysilane to be linked to the surface of the porous silica particle or the inside pores of the particle.

Further, since the alkoxysilane has a substituent to be introduced, the substituent may be introduced on the surface of the porous silica particle or inside the pores of the particle.

The above reaction may be performed by reacting porous silica particles dispersed in a solvent with alkoxysilane.

The solvent used may be water and/or an organic solvent. This organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethyl-methoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane, or the like, in particular, toluene may be used, but it is not limited thereto.

For example, the modification into a cationic substituent may be conducted by reacting the particles with alkoxysilane having a basic group, i.e., a nitrogen containing group such as amino or aminoalkyl. More particularly, N-[3-(Trimethoxysilyl)propyl]ethylenediamine, N1-(3-Trimethoxysilylpropyl)diethylenetriamine, (3-Aminopropyl)trimethoxysilane, N-[3-(Trimethoxysilyl)propyl]aniline, Trimethoxy[3-(methylamino)propyl]silane, 3-(2-Aminoethylamino)propyldimethoxymethylsilane, and the like may be used, but it is not limited thereto.

For example, the modification into an anionic substituent may be conducted by reacting the particles with alkoxysilane having an acidic group such as carboxyl, sufonic acid, thiol or the like. More particularly, (3-Mercaptopropyl) trimethoxysilane, and the like may be used, but it is not limited thereto.

The hydrophilicity may be introduced by reacting the particles with alkoxisilane having a hydrophilic functional group, for example, hydroxyl, carboxyl, amino, carbonyl, sulfhydryl, phosphate, thiol, ammonium, ester, imide, thioamide, keto, ether, indene, sulfonyl, polyethyleneglycol or the like. More particularly, N-[3-(Trimethoxysilyl)propyl] ethylenediamine, N1-(3-Trimethoxysilylpropyl)diethylenetriamine, (3-Aminopropyl)trimethoxysilane, (3-Mercaptopropyl)trimethoxysilane, Trimethoxy[3 -(methylamino) propyl]silane, 3-(2-Aminoethylamino) propyldimethoxymethylsilane, and the like may be used, but it is not limited thereto.

The hydrophobicity may be introduced by reacting the particles with alkoxysilane having a hydrophobic functional group such as substituted or non-substituted C1 to C30 alkyl, substituted or non-substituted C3 to C30 cycloalkyl, substituted or non-substituted C6 to C30 aryl, substituted or non-substituted C2 to C30 heteroaryl, halogen, C1 to C30 ester or a halogen-containing group. More particularly, Trimethoxy(octadecyl)silane, Trimethoxy-n-octylsilane, Trimethoxy(propyl)silane, Isobutyl(trimethoxy)silane, Trimethoxy(7-octen-1-yl)silane, Trimethoxy(3,3,3-trifluoropropyl)silane, Trimethoxy(2-phenylethyl)silane, Vinyltrimethoxysilane, Cyanomethyl, 3 -(trimethoxysilyl)propyl] trithiocarbonate, (3-Bromopropyl)trimethoxysilane, and the like may be used, but it is not limited thereto.

In addition, in order to increase a binding force of the particles to an insoluble (hydrophobic) bioactive substance, a hydrophobic substituent may be introduced inside the pore, and a hydrophilic substituent may be introduced on the surface of the particles in terms of ease of use and formulation, and substituents for binding other substances besides the bioactive substance may be introduced on the surface by the modification.

Further, the modification may be conducted in a combination mode. For instance, surface modification may be conducted twice or more on an external surface of the particle or inside the pores of the particle. In a particular example, the positively charged particle may be changed to have different surface characteristics by binding a compound containing a carboxyl group to silica particles having an amino group introduced therein via an amide bond, but it is not limited thereto.

The reaction of the particles with alkoxysilane may be conducted, for example, under heating.

In this case, the heating may be conducted, for example, at 80° C. to 180° C. For instance, the reaction may be conducted at 80° C. to 160° C., 80° C. to 150° C., 100° C. to 160° C., 100° C. to 150° C., 110° C. to 150° C., or the like within the above range, but it is not limited thereto.

Further, the reaction of the particle with alkoxysilane may be conducted, for example, for 4 to 20 hours. For instance, the reaction may be conducted for 4 to 18 hours, 4 to 16 hours, 6 to 18 hours, 6 to 16 hours, 8 to 18 hours, 8 to 16 hours, 8 to 14 hours, 10 to 14 hours, or the like within the above range, but it is not limited thereto.

With regard to the modification described above, a reaction temperature, a reaction time, an amount of the compound used for modification, etc. may be properly selected in consideration of degree of modification. More particularly, under different reaction conditions based on hydrophilicity, hydrophobicity and/or a charge level of the bioactive substance, hydrophilicity, hydrophobicity and/or the charge level of the porous silica particles may be adjusted, thereby controlling a release rate of the bioactive substance. For instance, once the bioactive substance is highly negatively charged at neutral pH, the reaction temperature or the reaction time may be increased or an amount of the compound treated may be increased in order for the porous silica particle to be highly positively charged, but it is not limited thereto.

With regard to the composition of the present invention, the porous silica particles may be prepared by, for example, processes for preparation of particles having small pores, pore expansion, surface modification and modification of inside the pores.

The processes for preparation of particles having small pores and for pore expansion may be performed by the above-described processes. Thereafter, washing and drying may be conducted.

If necessary, unreacted materials may be removed before washing.

For instance, such removal may be conducted by separating a supernatant through centrifugation.

The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

The washing process after preparation of the particles having small pores may be conducted by the method/under the conditions within the above-exemplified ranges, but it is not limited thereto.

The washing process after pore expansion may be conducted under more alleviated conditions, compared to the above-exemplified aspects. For instance, the washing may be conducted 3 times or less, but it is not limited thereto.

Modification of the surface of the particle and/or the inside pores of the particle may be performed by the above-described method. Surface modification of the particle and then modificaion of inside pores of the particle may be sequentially conduced in this order. Alternatively, a washing process of the particle may be further conducted between the above two processes.

When washing under more alleviated conditions after the preparation of particles having small pores and the pore expansion, a reacting solution such as the surfactant used in particle preparation and/or pore expansion is filled inside the pores. Therefore, the inside the pores is not modified during surface modification, instead, the surface only may be modified. Thereafter, the reacting solution inside the pores may be removed by washing the particles.

The particle washing between the surface modification and the modification of inside the pores may be conducted using water and/or an organic solvent. More particularly, since different types of materials are dissolved in different solvents, water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The washing may be conducted under centrifugation. The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

Alternatively, the washing may be conducted while filtering the particles through a filter without centrifugation. The filter used herein may contain pores having a pore diameter equal to or less than the diameter of the porous silica particles. By filtering the reacting solution, the particles only remain on the filter, and may be washed by pouring water and/or an organic solvent onto the filter.

During the washing, the water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at, for example, 20° C. to 100° C., but it is not limited thereto. Alternatively, the drying may be conducted under a vacuum condition.

Loading of the Bioactive Substance

The bioactive substance may be loaded on the surface of the particle and/or inside the pore.

For example, loading may be conducted by mixing the porous silica particle and a bioactive substance in a solvent.

The solvent used may be water and/or an organic solvent, and the organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.

The solvent used herein may further include phosphate buffered saline solution (PBS), simulated body fluid (SBF), borate-buffered saline, tris-buffered saline or the like.

A relative ratio of the porous silica particles and the bioactive substance is not particularly limited but may be in a ratio by weight of 1:0.05 to 0.8, for example, 1:0.05 to 0.7, 1:0.05 to 0.6, 1:0.1 to 0.8, 1:0.1 to 0.6, 1:0.2 to 0.8, 1:0.2 to 0.6, or the like within the above range.

Release of the Bioactive Substance

The porous silica particles may gradually release the bioactive substance carried therein over a long period of time.

The bioactive substance carried in the particles may be biodegraded and released. In this case, the particles may be slowly degraded to allow sustained release of the carried bioactive substance. This release may be controlled by, for example, adjusting the surface area, the particle diameter and/or the pore diameter of the porous silica particles, regulating substituents on the surface of the particle and/or inside the pores of the particle, surface compactness, or the like, but it is not limited thereto.

Further, the bioactive substance carried in the particles may escape from the porous silica particles and also be released while being diffused. This process may be influenced by a relationship between the porous silica particles and the bioactive substance, release environments of the bioactive substance or the like. Therefore, the release of the bioactive substance may be controlled by regulating the above conditions. For instance, the release of the bioactive substance may be controlled by strengthening or weakening a binding force between the porous silica particles and the bioactive substance through surface modification.

According to a more preferable example, when the carried bioactive substance is poorly soluble (hydrophobic), the surface of the particle and/or inside the pores of the particle may have a hydrophobic substituent, thus to increase the binding force of the particles to the bioactive substance, and thereby enabling sustained release of the bioactive substance. For instance, the above particles may be surface-modified with alkoxysilane having a hydrophobic substituent.

In the present disclosure, the term "poorly soluble" may include the meanings of "insoluble", "practically insoluble" or "only slightly soluble" to water, etc., which is a term defined in "Pharmaceutical Science" 18th Edition (published by U.S.P., Remington, Mack Publishing Company).

The poorly soluble bioactive substance may have, for example, a water-solubility of less than 10 g/L at 1 atm and 25° C., preferably less than 5 g/L and, more preferably less than 1 g/L, but it is not limited thereto.

When the carried bioactive substance is water-soluble (hydrophilic), the surface of the particle or inside the pores of the particle may have a hydrophilic substituent, thus to increase the binding force of the particles to the bioactive substance, and thereby enabling sustained release of the bioactive substance. For instance, the porous silica particles may be surface-modified with alkoxysilane having a hydrophilic substituent.

The water-soluble bioactive substance may have, for example, a water-solubility of 10 g/L or more at 1 atm and 25° C., but it is not limited thereto.

When the carried bioactive substance is charged, the surface of the particle and/or the inside the pores of the particle may be counter-charged, thus to increase the binding force between the porous silica particles and the bioactive substance, thereby enabling sustained release of the bioactive substance. For instance, the porous silica particles may be surface-modified with alkoxysilane having an acidic group or a basic group.

More particularly, if the bioactive substance is positively charged at neutral pH, the surface of the particle and/or the inside the pores of the particle may be negatively charged at neutral pH, thus to increase the binding force between the porous silica particles and the bioactive substance, and thereby enabling sustained release of the bioactive substance. For instance, the porous silica particles may be surface-modified with alkoxysilane having an acidic group such as carboxyl (—COOH), or sufonic acid group (—SO3H), etc.

Further, if the bioactive substance is negatively charged at neutral pH, the surface of the particle and/or the inside the pores of the particle may be positively charged at neutral pH, thus to increase the binding force between the porous silica particles and the bioactive substance, and thereby enabling sustained release of the bioactive substance. For instance, the porous silica particles may be surface-modified with alkoxysilane having a basic group such as amino, or other nitrogen-containing groups, etc.

The carried bioactive substance may be released over, for example, 7 days to 1 year or more depending upon release environments, the porous silica particles used for carrying the same and the like.

With regard to the composition of the present invention, the porous silica particles may be biodegradable and can be entirely degraded about 100%, therefore, the bioactive substance carried therein may be released to 100%.

Formulation and Administration of Bioactive Substance Carrier

The bioactive substance carrier of the present invention may be formulated for delivery through any route of administration. The "administration route" may include an aerosol, intranasal, oral, transmucosal, transdermal, parenteral or enteral route, however, may also refer to any administration known in the art, without limitation thereof.

The porous silica particles of the present invention may be biodegradable and degraded by up to 100%, thus may have excellent in vivo stability, and thereby being parenterally administrated, as well as manufactured as a formulated product for parenteral administration.

The "parenteral (non-oral)" route refers to an administration route generally associated with injection including intra-orbital, intra-ocular, infusion, intra-arterial, intra-articular, intra-cardiac, intra-dermal, intra-muscular, intra-peritoneal, intra-pulmonary, intra-spinal, intra-sternal, intra-thecal, intra-uterine, intravenous, subarachnoid, subcapsular, subcutaneous, transmucosal or transorgan administration. Through the parenteral route, the carrier may be in a solution or suspension form for infusion, injection or lyophilization. Through the enteric route, the bioactive substance carrier may be in any form of: tablets, gel capsules, sugar-coated tablets, syrups, suspensions, solutions, powders, granules, emulsions, microspheres or nanospheres, or lipid small vesicles or polymer small vesicles enabling controlled release. Typically, the carrier is administered by injection through one among intravenous or intra-peritoneal routes. Methods for administration through these routes are known to those skilled in the art.

The bioactive substance carrier according to the present invention may further include any pharmaceutically acceptable carrier. The "pharmaceutically acceptable carrier" as used in the present disclosure may refer to a pharmaceutically acceptable material, composition or vehicle, which is associated to carry or transport a compound of interest from a tissue, organ or portion of the body to other tissue, organ or portion of the body. For example, the carrier may be a liquid or solid filler, diluent, excipient, solvent or encapsulating material, or a combination thereof. Each of ingredients in the carrier should be "pharmaceutically acceptable", that is, capable of compatible with other ingredients of the formulation. Further, the carrier should be suitable for use when coming into contact with any of tissues or organs which can be in contact with the carrier. In fact, the carrier should not involve a risk of toxicity, irritation, allergic response, immunogenicity or any other complications which are much more significant than therapeutic advantages achieved by the carrier.

The bioactive substance carrier according to the invention may also be encapsulated, formed into tablets or prepared in an emulsion or syrup form for oral administration. The pharmaceutically acceptable solid or liquid carrier may be added to enhance or stabilize a composition, or to facilitate production of the composition. The liquid carrier may include syrup, peanut oil, olive oil, glycerin, saline, alcohol and water. The solid carrier may include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate alone or with a wax.

The bioactive substance carrier may be fabricated by typical pharmaceutical technique, involving: if necessary, pulverization, mixing, granulation and compression in a case of a table form; or pulverization, mixing and filling in a case of a hard gelatin capsule form. When using the liquid carrier, the formulated product may be in a syrup, elixir, emulsion or aqueous or non-aqueous suspension form. Such a liquid type formulation may be directly and orally administered, or be filled in a soft gelatin capsule.

The bioactive substance carrier according to the present invention may be delivered in a therapeutically effective amount. The exact therapeutically effective amount is an amount of the composition to obtain the most effective results for treatment efficacy on a given subject. This amount may vary depending on: characteristics of therapeutic compounds (including activity, pharmacokinetics, pharmacodynamics and biological activity), physiological conditions of the subjects (including age, gender, disease type and stage, general physical health conditions, reaction and type of medicament for a given dose), features of pharmaceutically acceptable carrier(s) in the formulation, administration routes, as well as may vary depending on a number of other factors that are not limited thereto. In clinical pharmacological fields, those skilled in the art will monitor the reaction of the subject for the administration of the compound and adjust the dosage based on the monitored results, thereby determining the therapeutically effective amount through routine experiments. For additional guidance, a literature will be incorporated herein (see [Remington: The Science and Practice of Pharmacy (Gennaro ed. 20th edition, Williams & Wilkins PA, USA) (2000)]).

An object to be administered with a drug carrier, that is, the carrier of the preset invention may include a mammal including a human, specifically, the human.

Prior to administration to the object, a formulation may be added to the formulated product. A liquid type formulation is preferable. The formulation may include, for example, oils, polymers, vitamins, carbohydrates, amino acids, salts, buffers, albumin, surfactants, extenders, or combinations thereof.

Carbohydrate formulations may include sugar or sugar alcohols, such as monosaccharides, disaccharides or polysaccharides, or water soluble glucans. Saccharides or glucans may include fructose, dextrose, lactose, glucose, mannose, sorbose, xylose, maltose, sucrose, dextran, pullulan, dextrin, alpha and beta cyclodextrin, soluble starch, hydroxyethyl starch, and carboxymethyl cellulose, or a mixture thereof "Sugar alcohol" is defined as a C4 to C8 hydrocarbon having an —OH group, may include galactitol, inositol, mannitol, xylitol, sorbitol, glycerol and arabitol. The above-mentioned sugar or sugar alcohols may be used alone or in combination thereof. If the sugar or sugar alcohol is soluble in an aqueous formulated product, there is no fixed limit in an amount to be used. In one embodiment, the sugar or sugar alcohol concentration may range from 1.0 w/v % to 7.0 w/v %, and more preferably from 2.0 to 6.0 w/v %.

Amino acid formulations may include levorotatory (L) forms of carnitine, arginine and betaine, however, other amino acids may also be added.

In some embodiments, the formulation may be a polymer which includes polyvinylpyrrolidone (PVP) with an average molecular weight of 2,000 to 3,000, or polyethyleneglycol (PEG) with an average molecular weight of 3,000 to 5,000.

Further, in order to minimize pH alteration in a solution before lyophilization or after re-constitution, it is preferable to use a buffer in the composition. The buffer may include citrate, phosphate, succinate and glutamate buffers or mixtures thereof, however, the majority of physiological buffers may also be used without limitation thereof. In some embodiments, a concentration thereof may range from 0.01 to 0.3 mol. Surfactants possibly added to the formulation are shown in European Patent Nos. 270,799 and 268,110.

Further, the carrier may be, for example, chemically modified by covalent conjugation to the polymer, in order to increase circulation half-life. Preferred polymers and methods to attach the carrier to peptides are disclosed in U.S. Pat. Nos. 4,766,106; 4,179,337; 4,495,285; and 4,609,546, the contents of which are entirely incorporated herein by reference. Preferred polymers may include polyoxyethylated polyols and polyethylene glycol (PEG). The PEG is soluble in water at room temperature, and in some embodiments, has an average molecular weight of 500 to 40,000, 2000 to 20,000 or 3,000 to 12,000. In some embodiments, the PEG has at least one hydroxyl group, for example, a terminal hydroxyl group. The hydroxyl group may be activated so as to react with a free amino group on an inhibitor. However, the type and amount of a reactor may vary so as to achieve PEG/antibodies which are covalently conjugated according to the present invention.

In addition, the water-soluble polyoxyethylated polyols may be useful in the present invention. These may include, for example, polyoxyethylated sorbitol, polyoxyethylated glucose, polyoxyethylated glycerol (POG) and the like. The POG is preferably used. One reason is that a glycerol backbone of the polyoxyethylated glycerol is mono-, di- or triclyceride, which is naturally derived, that is, same to the backbone in an animal or human. Thus, this branch is not necessarily considered to be a foreign agent in the body. The POG has a molecular weight in the same range as of the PEG. A structure of the POG is disclosed in a literature [Knauf et al., 1988, J. Bio. Chem. 263: 15064-15070], and discussions on POG/IL C2 conjugate are found in U.S. Pat. No. 4,766,106, the content of which are entirely incorporated herein by reference.

After the liquid bioactive substance carrier is manufactured, the carrier may be lyophilized to prevent degradation and to preserve sterility. Methods for lyophilization of a liquid composition are known to those skilled in the art. Immediately before using, the carrier may be reconstituted in a sterile diluent (e.g., Ringer's solution, distilled water, or sterile saline) that may include additional ingredients. Upon the reconstitution, the carrier is administered to the subject using any method known to those skilled in the art.

Use of Bioactive Substance Carrier

The bioactive substance carrier described above may include a drug and porous silica particles, and the present invention provides a use of the porous silica particles described above in a process for manufacturing the bioactive substance carrier.

As described above, the porous silica particles according to the present invention may be biodegradable and slowly degraded in vivo, thus to release the carried bioactive substance in a sustained manner, and thereby being used in the manufacture of a sustained-release type bioactive substance carrier.

Details of physical properties, specifications and surface modification of the porous silica particles may be within the range illustrated above, and the porous silica particles may be those manufactured by the method under the conditions within the range illustrated above.

EXAMPLE

1. Preparation of Porous Silica Particles
(1) Preparation of Porous Silica Particles
1) Preparation of Small Pore Particles 960 mL of distilled water and 810 mL of MeOH were put in a 2L round bottom flask. After putting 7.88 g of CTAB in the flask, 4.52 mL of 1M NaOH was quickly added to the flask under agitation. After forming a homogenous mixture while stirring for 10 minutes, 2.6 mL of TMOS was added. After stirring for 6 hours and homogenously mixing, the mixture was aged for 24 hours.

Thereafter, the reaction solution was centrifuged at 25° C. and 8000 rpm for 10 minutes to remove a supernatant, followed by further centrifugation at 25° C. and 8000 rpm for 10 minutes and washing with ethanol and distilled water, alternately, five times.

Then, the product was dried in an oven at 70° C. to yield 1.5 g of powder type small pore silica particles (with a mean pore diameter of 2 nm and a particle diameter of 200 nm).

2) Pore Expansion 1.5 g of small pore silica particles were added to 10 ml of ethanol, and ultrasonic dispersion was performed. Then, 10 ml of water and 10 ml of trimethyl benzene (TMB) were added to the reaction solution, followed by ultrasonic dispersion.

Then, the dispersion was placed in an autoclave and reacted at 160° C. for 48 hours.

The reaction was initiated at 25° C., continued while raising the temperature at a rate of 10° C./min, and then, the reacted dispersion was gradually cooled in the autoclave at a rate of 1 to 10° C./min.

The cooled reaction solution was subjected to centrifugation at 25° C. and 8000 rpm for 10 minutes to remove the supernatant, followed by further centrifugation at 25° C. and 8000 rpm for 10 minutes and washing with ethanol and distilled water, alternately, five times.

Then, the product was dried in an oven at 70° C. to yield powder type small pore silica particles (with a mean pore diameter of 10 to 15 nm and a particle diameter of 200 nm).

3) Calcinations

The porous silica particles prepared in section 2) above were put in a glass vial, heated at 550° C. for 5 hours, and after completion of the reaction, slowly cooled down to room temperature, thereby yielding particles.

(2) Preparation of Porous Silica Particles

Porous silica particles were prepared in the same manner as described in Example 1-(1) above, except that the reaction conditions were altered into at 140° C. and 72 hours.

(3) Preparation of Porous Silica Particles (10L Scale)

Porous silica particles were prepared in the same manner as described in Example 1-(1) above, except that a 5-fold larger vessel was used and each of the materials was used with 5-fold volume.

(4) Preparation of Porous Silica Particles (Particle Diameter 300 nm)

Porous silica particles were prepared in the same manner as described in section (1) above, except that 920 ml of distilled water, and 850 ml of methanol were used in the preparation of small pore particles.

(5) Preparation of Porous Silica Particles (Particle Diameter 500 nm)

Porous silica particles were prepared in the same manner as described in section (1) above, except that 800 ml of distilled water, 1010 ml of methanol and 10.6 g of CTAB were used in the preparation of small pore particles.

(6) Preparation of Porous Silica Particles (Particle Diameter of 1000 nm)

Porous silica particles were prepared in the same manner as described in section (1) above, except that 620 ml of distilled water, 1380 ml of methanol and 7.88 g of CTAB were used in the preparation of small pore particles.

(7) Preparation of Porous Silica Particles (Pore Diameter of 4 nm)

Porous silica particles were prepared in the same manner as described in section (1) above, except that 2.5 mL of TMB was used upon the pore expansion.

(8) Preparation of Porous Silica Particles (Pore Diameter of 7 nm)

Porous silica particles were prepared in the same manner as described in section (1) above, except that 4.5 mL of TMB was used upon the pore expansion.

(9) Preparation of Porous Silica Particles (Pore Diameter of 17 nm)

Porous silica particles were prepared in the same manner as described in section (1) above, except that 11 mL of TMB was used upon the pore expansion.

(10) Preparation of Porous Silica Particles (Pore Diameter of 23 nm)

Porous silica particles were prepared in the same manner as described in section (1) above, except that 12.5 mL of TMB was used upon the pore expansion.

(11) Preparation of Porous Silica Particles (Double Modification)

1) Preparation of Small Pore Particles

In the same manner as described in Example (1)-1, small pore particles were prepared.

2) Pore Expansion

In the same manner as described in Example (1)-2, the small pore particles were reacted with TMB, then cooled down and centrifuged to remove the supernatant. Then, under the same conditions as in Example (1)-2, centrifugation was performed, followed by washing with ethanol and distilled water, alternately, three times. Thereafter, the reaction product was dried under the same conditions as in Example (1)-2, thereby yielding powder type porous silica particles (with a pore diameter of 10 to 15 nm, and a particle diameter of 200 nm).

3) Surface Modification

After 0.8 g to 1 g of the porous silica particles with expanded pores were dispersed in 50 mL of toluene, 5 mL of (3-aminopropyl)triethoxysilane was put in the dispersion and heated at 120° C. for 12 hours while refluxing. This process was performed by, after the above washing and drying processes, dispersing 1 mL of triethyleneglycol (PEG3, 2-[2-(2-methoxyethoxy)ethoxy]acetic acid), 100 mg of EDC (1-ethyl-3-(3-dimethylaminopropyl)carbodiimide) and 200 mg of N-Hydroxysuccinimide (NHS) in 30 mL of PBS, and conducting a reaction for 12 hours while stirring at room temperature. Then, the reaction product was subjected to washing and drying.

Since the previously reaction solution remains inside the pores, the inside the pore was not modified.

4) Washing of Pore Inside 800 mg of surface-modified particle powders were dissolved in 40 ml of 2M HCl/ethanol, followed by refluxing while vigorously stirring for 12 hours.

Then, the chilled reaction solution was centrifuged at 8000 rpm for 10 minutes to remove the supernatant, further centrifuged at 25° C. for and 8000 rpm for 10 minutes, followed by washing with ethanol and distilled water, alternately, five times.

Thereafter, the reaction product was dried in an oven at 70° C., thereby yielding powder type porous silica particles.

5) Modification of Pore Inside (i) A propyl group was introduced inside the pore in the same manner as Example 2-(2)-1 to be described below.

(ii) An octyl group was introduced inside the pore in the same manner as Example 2-(2)-2 to be described below.

2. Surface Modification (1) Charging to a Positive Charge

1) Particles Having a Particle Diameter 300 nm

The porous silica particles in Example 1-(4) were reacted with (3-Aminopropyl)triethoxysilane (APTES) so as to be positively charged.

Specifically, 100 mg of porous silica particles was dispersed in 10 ml toluene in a 100 mL round bottom flask by a bath sonicator. Then, 1 mL of APTES was added, and the reaction mixture was reacted at 130° C. while stirring at 400 rpm for 12 hours.

After the reaction, the reaction product was slowly cooled down to room temperature, centrifuged at 8000 rpm for 10 minutes to remove the supernatant, further centrifuged at 25° C. and 8000 rpm for 10 minutes, followed by washing with ethanol and distilled water, alternately, five times.

Thereafter, the reaction product was dried in an oven at 70° C., thereby yielding powder type porous silica particles having amino groups on the surface of the particle and inside the pore.

2) Particles with Particle Diameter of 200 nm (i) Modification was performed in the same manner as described in Example 2-(1)-1 above, except that the porous silica particles in Example 1-(1) were reacted with (3-aminopropyl)triethoxysilane (APTES) so as to be positively charged, 0.4 ml of APTES was added and the reaction was conducted for 3 hours.

(ii) Modification was performed in the same manner as described in Example 2-(1)-1 above, except that the porous silica particles in Example 1-(9) were reacted with (3-aminopropyl)triethoxysilane (APTES) so as to be positively charged.

(iii) Modification was performed in the same manner as described in Example 2-(1)-1 above, except that the porous silica particles in Example 1-(10) were reacted with (3-aminopropyl)triethoxysilane (APTES) so as to be positively charged.

(2) Introduction of Hydrophobic Group

1) Propyl Group

Modification was performed in the same manner as described in Example 2-(1) above, except that the porous silica particles in Example 1-(1) were reacted with trimethoxy(propyl)silane to introduce propyl groups into the surface of the particle and inside the pores, 0.35 ml of trimethoxy(propyl)silane was added in place of APTES, and the reaction was conducted for 12 hours.

2) Octyl Group

Modification was performed in the same manner as described in Example 2-(1) above, except that the porous silica particles in Example 1-(1) were reacted with trimethoxy-n-octylsilane to introduce propyl groups into the surface of the particle and inside the pores, 0.5 ml of trimethoxy-n-octylsilane was added in place of APTES, and the reaction was conducted for 12 hours.

(3) Charging to Negative Charge

1) Carboxyl Group

Modification was performed in the same manner as described in Example 2-(1)-1) above, except that the porous silica particles in Example 1-(1) were reacted with succinic anhydride so as to be negatively charged, dimethyl sulfoxide (DMSO) was used instead of toluene, 80 mg of succinic anhydride was added in place of APTES and reacted at room temperature while stirring for 24 hours, and DMSO was used for washing instead of the distilled water.

2) Thiol Group

Modification was performed in the same manner as described in Example 2-(1)-1) above, except that 1.1 mL of MPTES was used instead of APTES.

3) Sulfonic Acid Group

Modification was performed in the same manner as described in Example 2-(1)-1) above, except that 100 mg of the porous silica particles in section (3)-2) were dispersed in 1 mL of 1M sulfuric acid solution and 20 mL of 30% hydrogen peroxide and agitated at room temperature to induce oxidation reaction, which in turn has oxidized a thiol group into a sulfonic acid group. Thereafter, the reaction product was washed and dried in the same manner as described in Example 2-(1)-1).

3. Bioactive Substance Loading (1) Doxorubicin

The porous silica particles in Example 1-(1) were loaded with doxorubicin.

Specifically, after mixing 5 mg of porous silica particle powders and 2 mg of doxorubicin in distilled water, the mixture was allowed to stand at room temperature for 1 hour.

(2) Irinotecan

After dispersing 5 mg of porous silica particle powders having negative charge in Example 2-(3)-1) in 1 mL of 1×PBS, 2 mg of irinotecan was added to the dispersion and dispersed for 15 minutes, and the mixture was allowed to stand at room temperature for 1 hour.

(3) Sorafenib

The porous silica particles in Example 1-(11)-5)(i) were loaded with sorafenib.

Specifically, after mixing 5 mg of porous silica particle powders and 2 mg of sorafenib in 1 ml of deionized water/ethanol having a mixing ratio of 5:5 (volume ratio), the mixture was incubated at room temperature for 1 hour. Thereafter, the product was washed with 1 ml of deionized water three times.

(4) Retinoic Acid 1 ml of retinoic acid solution (50 mM ethanol) was added to 100 µg of the porous silica particle powders in Example 2-(1)-2)(i), followed by standing at room temperature for 4 hours. Thereafter, the product was washed with 1 ml of ethanol three times.

(5) p53 Peptides

The porous silica particles used herein was the particles in Example 1-(11)-5)(i).

p53 peptide used herein mimicked a portion of p53 protein sequence associated with cell death (apoptosis) mechanism. The mimic sequence relates to a sequence of the hydrophobic secondary helical structure wherein the p53 protein is combined with hMDM2 protein. Thus, the p53 peptide acts as an antagonist of the hMDM2 protein.

An amino acid sequence of the p53 peptide (Cal. m.w. 2596.78, found by MALDI-TOF 2597.92) is represented by the following Formula 1 (N-terminal→C-terminal).

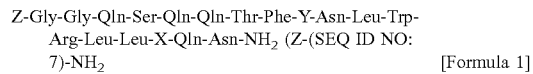

[Formula 1]

(wherein X is a non-natural amino acid introduced with an azide functional group and denotes 2-amino-5-azido-pentanoic acid; and Y is a non-natural amino acid introduced with an alkyne functional group wherein 4-pentynoic acid is introduced at a side chain of D-Lys;

X and Y are linked to form a triazole functional group through azide-alkyne cycloaddition (or click reaction) with a reaction ring; and Z denotes 5(6)-carboxy fluorescein (FAM)).

1.3 mg (500 nmole) of p53 peptide was dissolved in 100 µl of DMSO and mixed with 5 mL of a solution containing 5 mg porous silica particle powder in a 15 mL conical tube, followed by incubation at room temperature for 12 hours.

The porous silica particles loaded with p53 peptide were subjected to centrifugation (9289 rcf, 8500 rpm, 20 minutes, and 15 mL conical tube) and washing with water three times, thereby being purified.

(6) siRNA 21 base pair duplex siRNA that targets green fluorescent protein (GFP) were synthesized upon request and purchased from Bioneer Co. Ltd. (sequence: sense; 5'-GGCUACGU-CCAGGAGCGCACC-3' (SEQ ID NO: 1), antisense; 5'-UGCGCUCCUGGACGUAGCCUU-3' (SEQ ID NO: 2))

10 µg of the porous silica particles in Example 2-(1)-2)(ii) and 50 pmol of siRNA were admixed in 1×PBS condition, followed by standing at room temperature for 30 minutes to complete loading.

(7) Plasmid DNA 6.7 k base pair of plasmid DNA (SEQ ID NO: 5) designed to express GFP in pcDNA3.3 backbone was produced from bacteria and used after the purification.

10 µg of the porous silica particles in Example 2-(1)-2) (iii) and 0.25 µg of plasmid DNA were admixed in 1×PBS condition, followed by standing at room temperature for 30 minutes to complete loading.

(8) Linear DNA 1.9 k base pair of linear DNA (SEQ ID NO: 6) designed in a sequential order of Forward primer—CMV promotor13 eGFP cDNA-Reverse primer and obtained by PCR amplification were used.

12.5 μg of the porous silica particles in Example 2-(1)-2)(iii) and 0.25 μg of linear DNA were admixed in 1×PBS condition, followed by standing at room temperature for 30 minutes to complete loading.

(9) Protein

1) BSA

100 μg of the porous silica particle powders in Example 2-(1)-2)(ii) and 10 μg of BSA (Sigma Aldrich, A6003) were admixed in 200 μl of 1×PBS, followed by incubation at room temperature for 1 hour.

2) IgG

100 μg of the porous silica particle powders in Example 2-(1)-2)(ii) and 10 μg of anti-twist IgG (Santacruz, sc-81417) were admixed in 200 μl of 1×PBS, followed by incubation at room temperature for 1 hour.

3) RNase A

100 μg of the porous silica particle powders in Example 1-(9) and 10 μg of RNase A (Sigma Aldrich, R6513) were admixed in 200 μl of 1×PBS, followed by incubation at room temperature for 1 hour.

4) Cas9

40 μg of the porous silica particle powders in Example 2-(1)-2)(i), 4 μg of Cas9 protein (SEQ ID NO: 3) and 2.25 μg of guide BSA (SEQ ID NO: 4) were admixed in 10 μl of 1×PBS, followed by incubation at room temperature for 1 hour.

Experimental Example

1. Identification of Particle Formation and Pore Expansion

According to observation of the small pore particles and the porous silica particles prepared in Examples 1-(1) to (3) by a microscope, it was determined whether the small pore particles were uniformly generated, the pores were sufficiently expanded, and the porous silica particles were uniformly formed (FIGS. 1 to 4).

Figure 2:
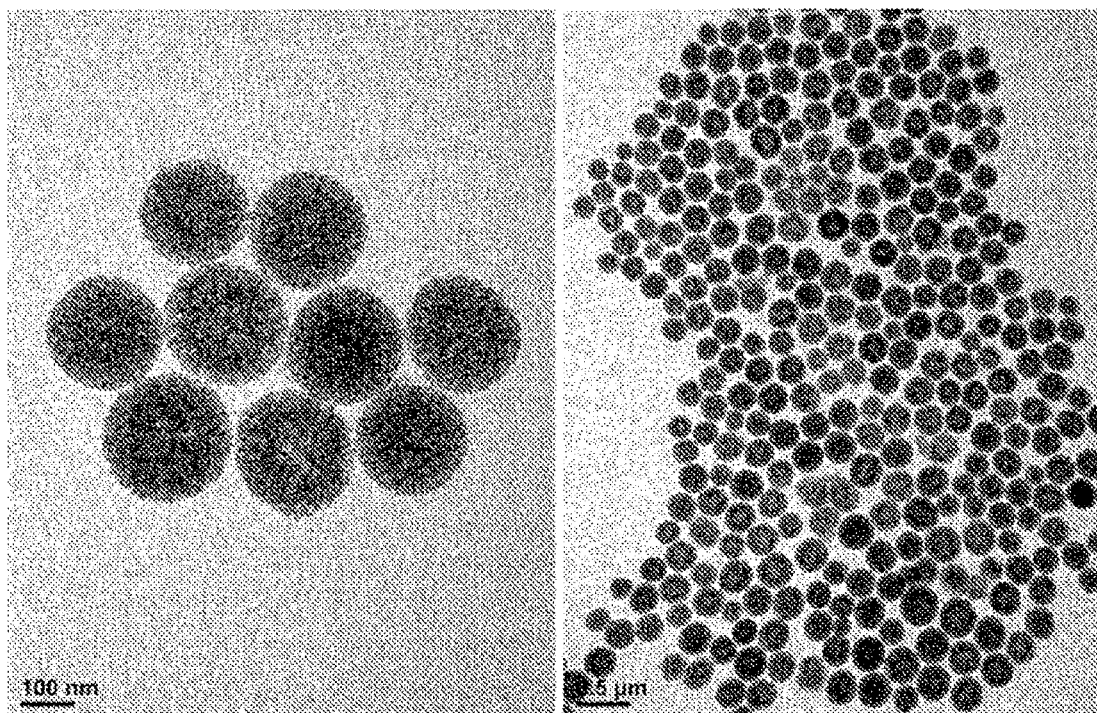
FIG. 2 is microphotographs showing porous silica particles according to one embodiment of the present invention.

FIG. 1 is photographs showing the porous silica particles in Example 1-(1), and FIG. 2 is photographs showing the porous silica particles in Example 1-(2), demonstrating that spherical porous silica particles with sufficiently expanded pores were uniformly formed.

Figure 3:
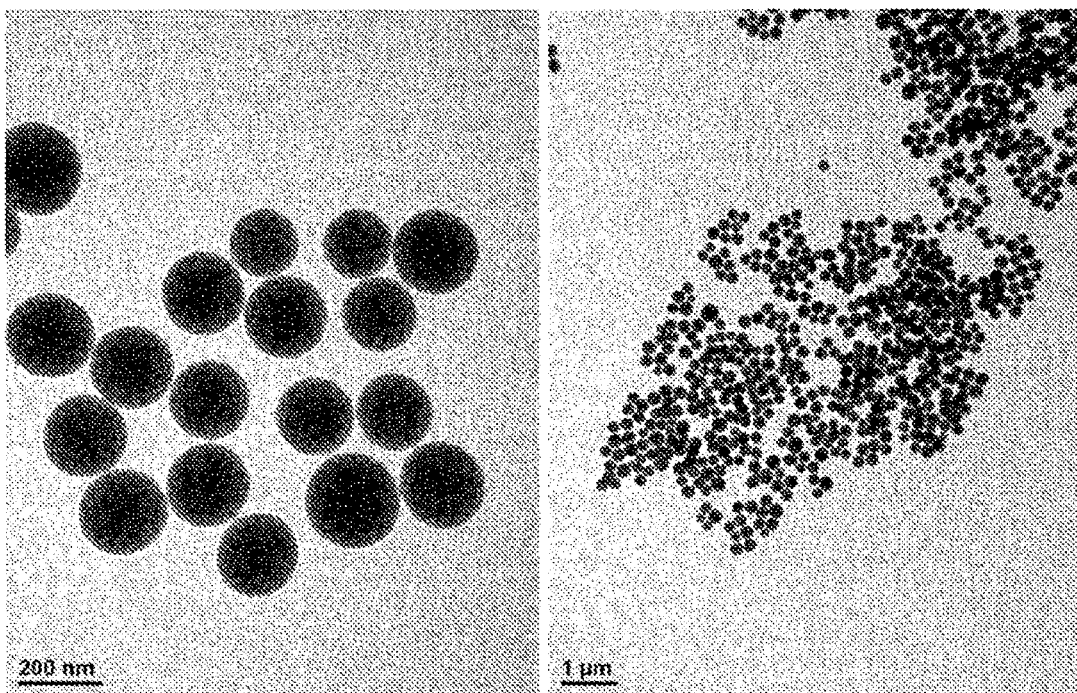
FIG. 3 is microphotographs showing microporous particles generated during production of the porous silica particles according to one embodiment of the present invention.
Figure 4:
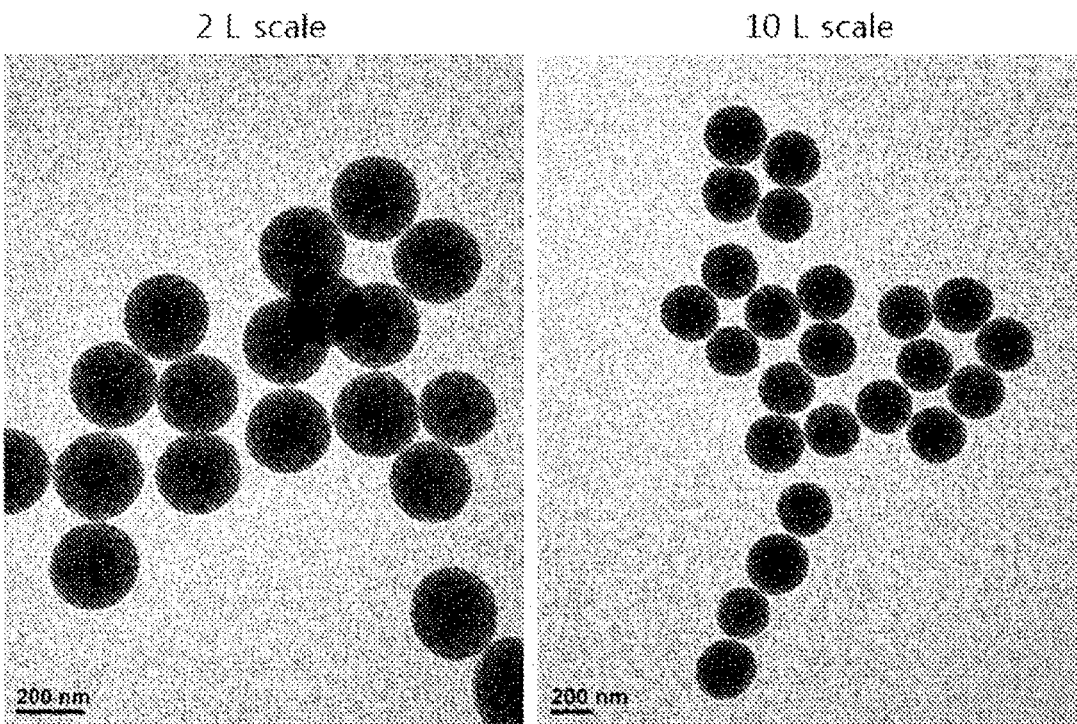
FIG. 4 is microphotographs showing microporous particles according to one embedment of the present invention.

FIG. 3 is photographs showing the small pore particles in Example 1-(1), and FIG. 4 is photographs showing comparison of the small pore particles in Examples 1-(1) and 1-(3), demonstrating that spherical small pore particles were uniformly formed.

2. Calculation of BET Surface Area and Pore Volume

With regard to the small pore particles in Example 1-(1) and the porous silica particles in Examples 1-(1), (7), (8) and (10), surface area and pore volume were calculated. The surface area was calculated by a Brunauer-Emmett-Teller (BET) method, and a distribution of pore volumes was calculated by a Barrett-Joyner-Halenda (BJH) method.

Figure 5:
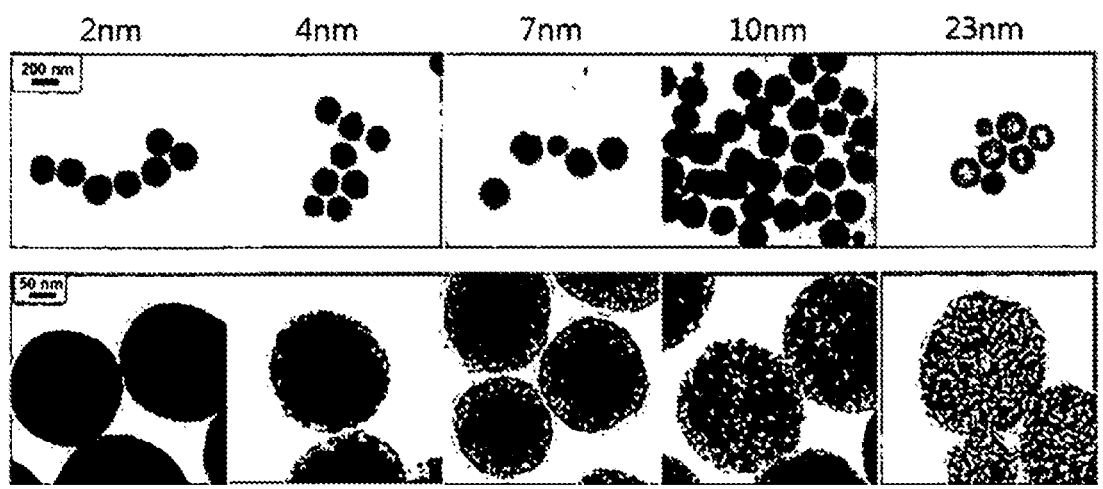
FIG. 5 is microphotographs showing the porous silica particles by pore diameter according to one embodiment of the present invention Herein, a degradable delivery vehicle (DDV) refers to an illustrative particle, wherein the numeral in parentheses denotes a particle diameter and the numeral in the subscript denotes a pore diameter. For example, $DVD(200)_{10}$ means the illustrative particle having a particle diameter of 200 nm and a pore diameter of 10 nm.

The microphotographs of the respective particles are shown in FIG. 5, and results of the calculation are shown in Table 1 below.

TABLE 1

| Section | Pore diameter (nm) | BET surface area (m²/g) | Pore volume (mL/g) |
| --- | --- | --- | --- |
| Small pore particles in Example 1-(1) | 2.1 | 1337 | 0.69 |
| Example 1-(7) | 4.3 | 630 | 0.72 |
| Example 1-(8) | 6.9 | 521 | 0.79 |
| Example 1-(1) | 10.4 | 486 | 0.82 |
| Example 1-(10) | 23 | 396 | 0.97 |

3. Identification of Biodegradability of Porous Silica Particles

Figure 6:
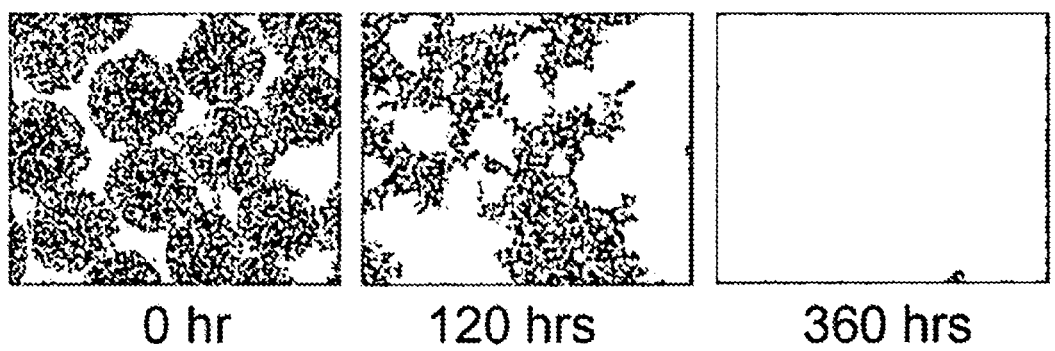
FIG. 6 is microphotographs illustrating identification of biodegradability of the porous silica particles according to one embodiment of the present invention.

In order to identify biodegradability of the porous silica particles in Example 1-(1), a biodegradation degree in SBF (pH 7.4) at 37° C. was observed by a microscope at 0 hour, 120 hours and 360 hours, and results thereof are shown in FIG. 6.

Referring to FIG. 6, it could be seen that the porous silica particles were biodegraded and almost degraded after 360 hours.

4. Measurement of Absorbance Ratio of Porous Silica Particles

An absorbance ratio by time was determined according to Equation 1 below.

$$A_t/A_0 \quad \text{[Equation 1]}$$

(wherein $A_0$ denotes an absorbance of porous silica particles measured after putting 5 ml of a suspension including 1 mg/ml of the porous silica particles in a cylindrical permeable membrane having pores with a diameter of 50 kDa, wherein 15 ml of a solvent in contact with the permeable membrane and substantially identical to the suspension is present outside the permeable membrane, inner and outer portions of the permeable membrane are horizontally agitated at 37° C. and 60 rpm, the suspension has pH 7.4, and wherein $A_t$ denotes an absorbance of the porous silica particles measured 't' hour after the measurement of $A_0$).

Specifically, 5 mg of porous silica particle powders were dissolved in 5 ml of SBF (pH 7.4). Then, the prepared 5 ml porous silica particle solution was put in a permeable membrane having pores with a diameter of 50 kDa shown in FIG. 7. 15 ml of SBF was added to an outer membrane and SBF in the outer membrane was changed every 12 hours. Degradation of the porous silica particles was performed at 37° C. under horizontal agitation at 60 rpm.

Thereafter, the absorbance was measured by UV-vis spectroscopy and analyzed at λ=640 nm.

(1) Measurement of Absorbance Ratio

Figure 8:
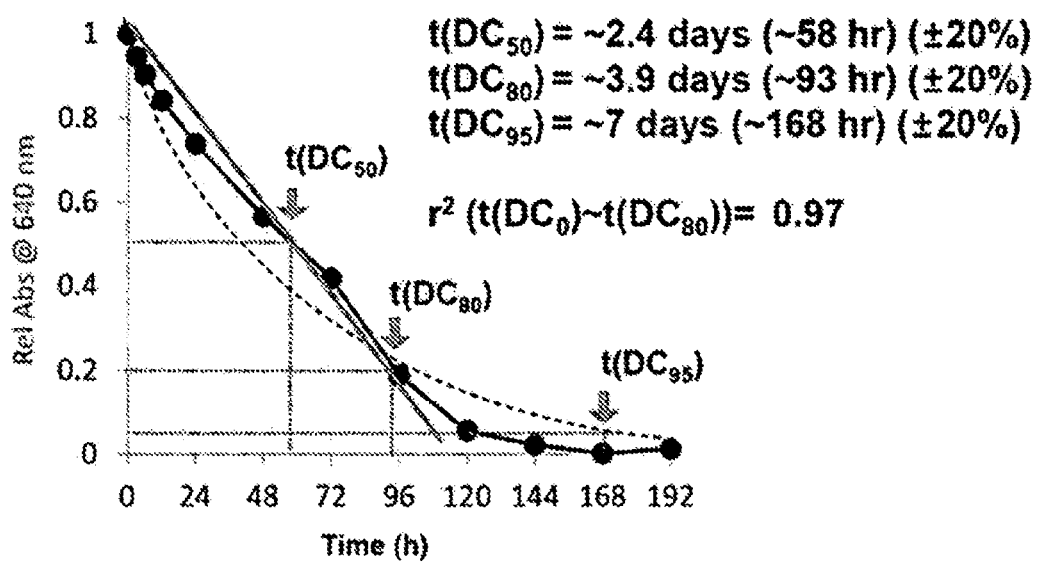
FIG. 8 illustrates a reduction in absorbance over time of the porous silica particles according to one embodiment of the present invention.

An absorbance ratio of the porous silica particles in Example 1-(1) was measured according to the above method, and results thereof are shown in FIG. 8.

Referring to FIG. 8, 't' at which the absorbance ratio reaches ½ was about 58 hours, and it could be seen that the porous silica particles are very slowly degraded.

(2) Absorbance by Particle Diameter

Figure 9:
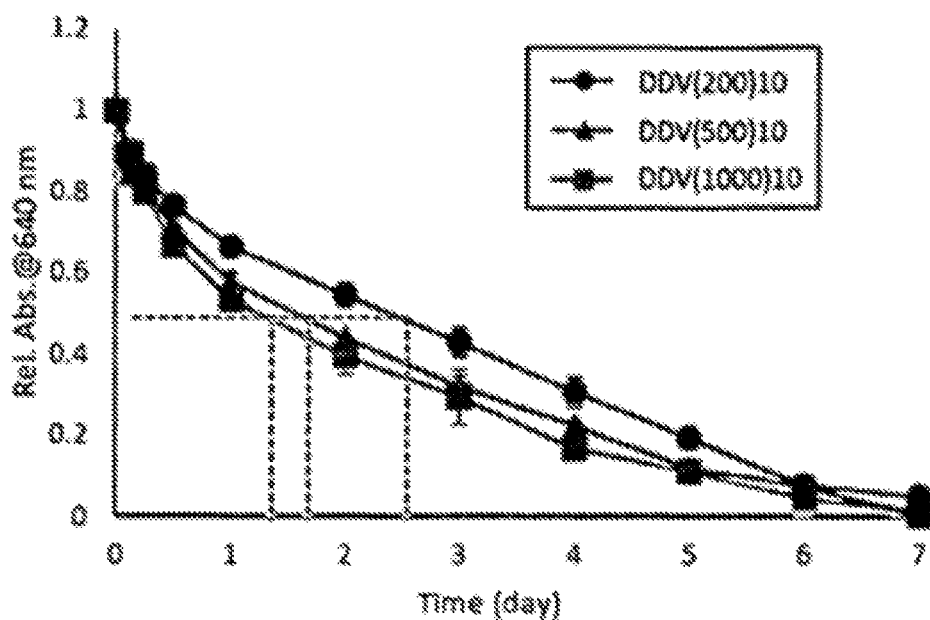
FIG. 9 illustrates a reduction in absorbance by particle diameter over time of the porous silica particles according to one embodiment of the present invention.

An absorbance of the porous silica particles in Examples 1-(1), (5) and (6), respectively, was measured by the above Equation 1, and results thereof are shown in FIG. 9 (with SBF used as a suspension and a solvent).

Referring to FIG. 9, it could be seen that 't' is decreased with an increase in the diameter of particles.

(2) Absorbance by Average Pores Diameter

Figure 10:
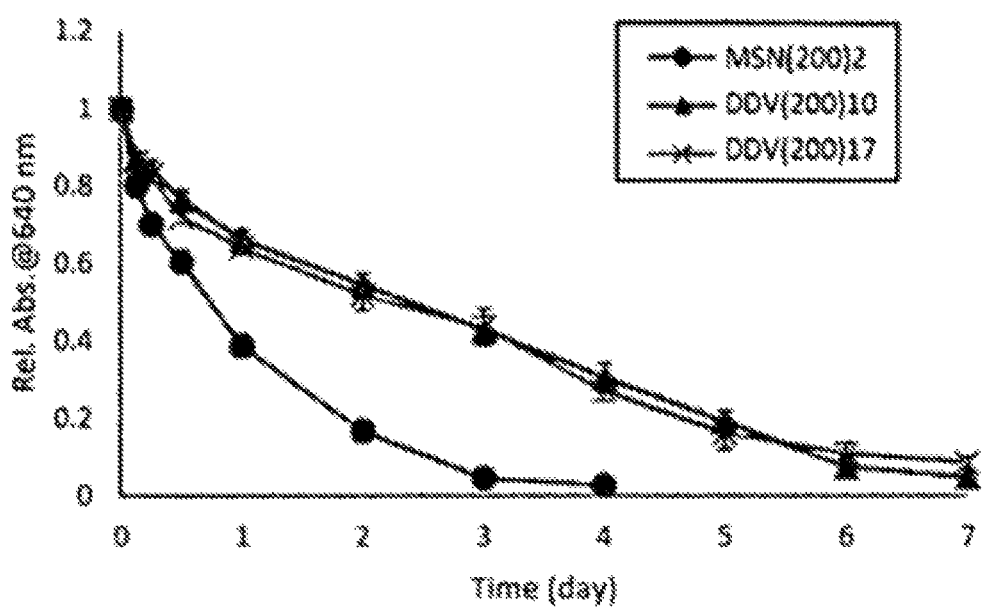
FIG. 10 illustrates a reduction in absorbance by pore diameter over time of the porous silica particles according to one embodiment of the present invention.

An absorbance of the porous silica particles in Examples 1-(1) and (9), respectively, as well as an absorbance of the small pore silica particles in Example 1-(1) as a control group were measured by the above Equation 1, and results thereof are shown in FIG. 10 (with SBF used as a suspension and a solvent).

Referring to FIG. 10, it could be seen that 't' of the porous silica particles in the examples is considerably larger than the control group.

(3) Absorbance by pH

An absorbance by pH of the porous silica particles in Example 1-(4) was measured. The absorbance was measured in SBF and Tris at pH 2, 5 and 7.4, and results thereof are shown in FIG. 11.

Figure 11:
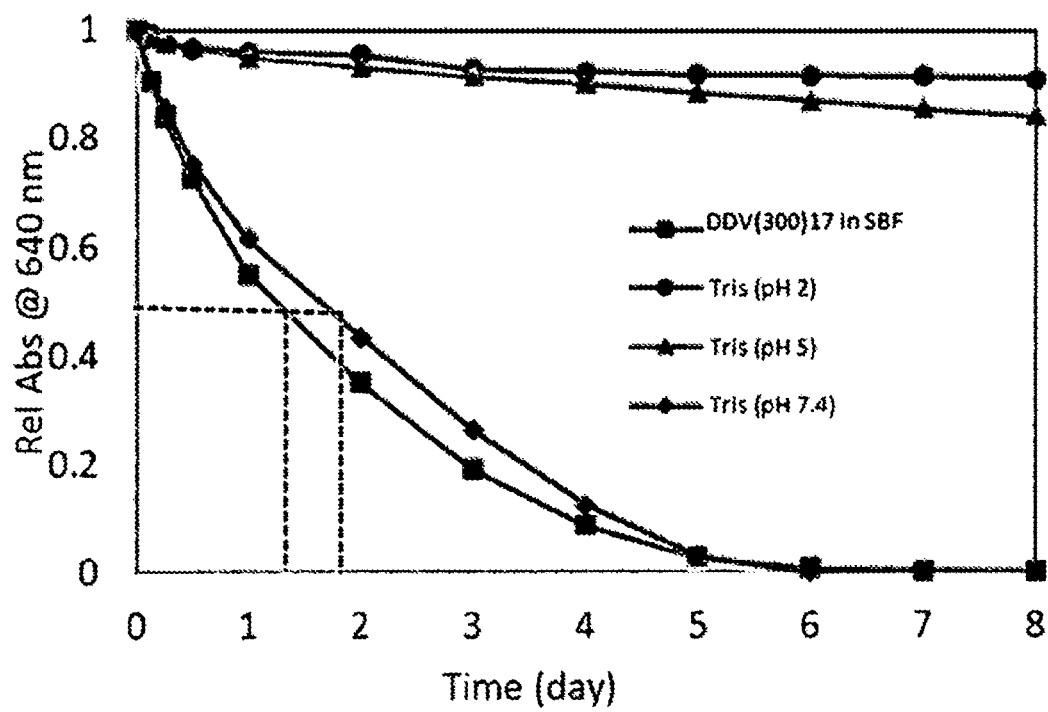
FIG. 11 illustrates a reduction in absorbance by pH in an environment over time of the porous silica particles according to one embodiment of the present invention.

Referring to FIG. 11, it could be seen that, although there is a difference in 't' by pH, 't' at which all of absorbance ratios reach ½ was 24 or more.

(4) Charging

Figure 12:
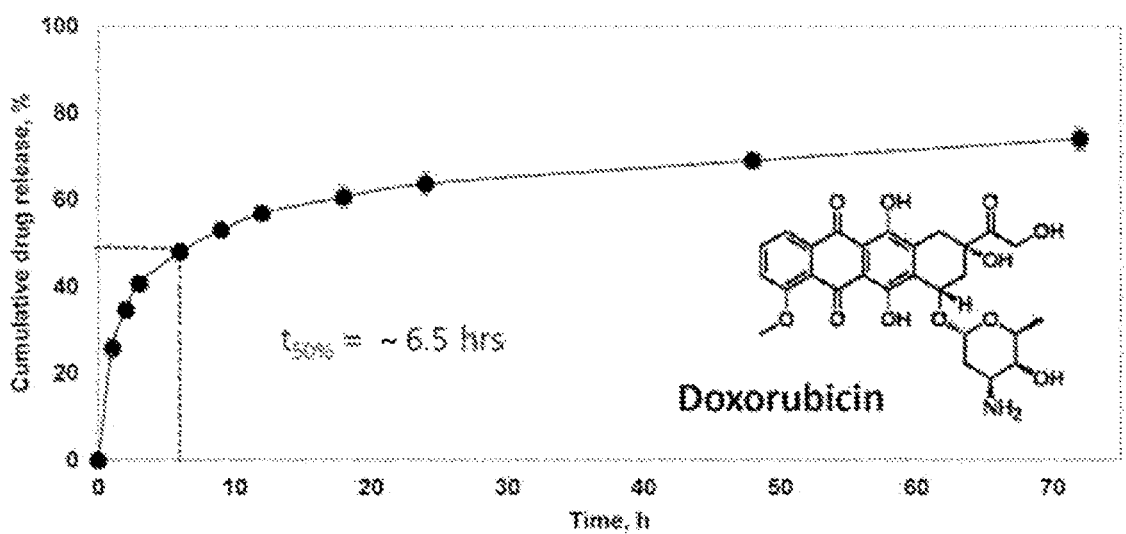
FIG. 12 illustrates a reduction in absorbance over time of the porous silica particles according to one embodiment of the present invention.

An absorbance of the porous silica particles in Example 2-(1)-1) was measured, and results thereof are shown in FIG. 12 (Tris (pH 7.4) used as a suspension and a solvent).

Referring to FIG. 12, it could be seen that positively charged particles also have 't' of 24 or more when the absorbance ratios reach ½.

5. Release of Bioactive Substance (1) Doxorubicin 0.5 mg of porous silica particles loaded with doxorubicin (0.1 mg) was dispersed in PBS. This solution was maintained in a dynamic condition for horizontal agitation at 37° C. and 200 rpm. The doxorubicin-loaded porous silica solution was settled by a centrifugal separator at each time point, an absorbance of the supernatant (λab=480 nm) was measured to determine an amount of released doxorubicin, and results thereof are shown in FIG. 13.

Figure 13:
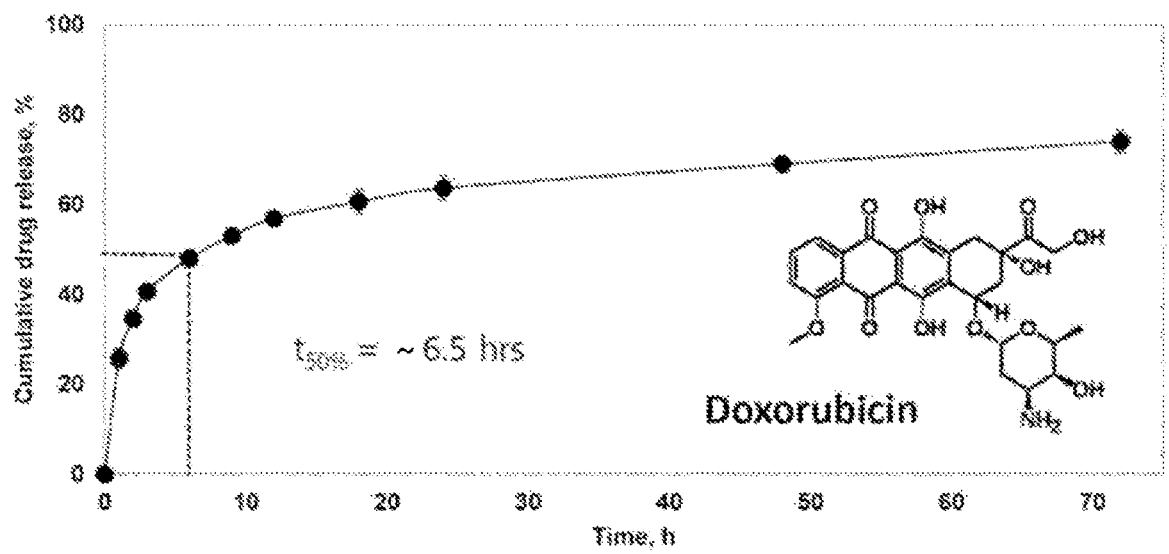
FIGS. 13 to 17 illustrate release profiles over time of bioactive substances, respectively, supported on the porous silica particles according to one embodiment of the present invention.

Referring to FIG. 13, it could be seen that doxorubicin was loaded on the surface of the particle with a relatively weak bonding force and was relatively quickly released due to high solubility in PBS, as well as the bioactive substance was continuously released over 70 hours or more.

(2) Irinotecan 1 mg of porous silica particles loaded with irinotecan (0.2 mg) was dispersed in 1 mL of human plasma. This solution was maintained in a dynamic condition for horizontal agitation at 37° C. and 200 rpm. The irinotecan-loaded porous silica solution was settled by a centrifugal separator at each time point, an absorbance of the supernatant (λab=255 or 278 nm) was measured to determine an amount of released irinotecan, and results thereof are shown in FIG. 14.

Figure 14:
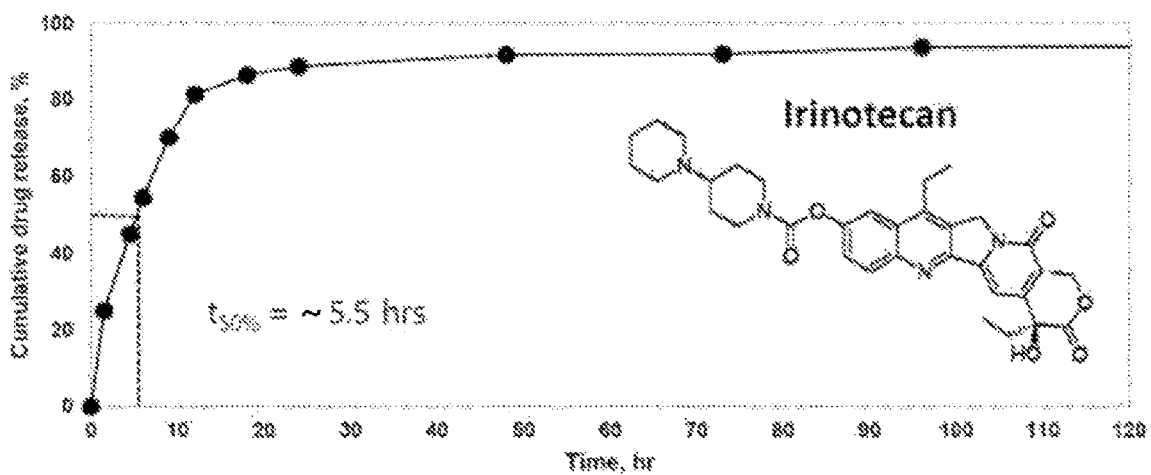

Referring to FIG. 14, it could be seen that irinotecan was released by about 50% after 5.5 hours, and the bioactive substance was continuously released over 120 hours or more.

(3) Sorafenib 1 mg of porous silica particles loaded with sorafenib (0.1 mg) was dispersed in 10 mL of 1×PBS mL. This solution was maintained in a dynamic condition for horizontal agitation at 37° C. and 200 rpm. The sorafenib-loaded porous silica solution was settled by a centrifugal separator at each time point, an absorbance of the supernatant (λab=270 nm) was measured to determine an amount of released sorafenib, and results thereof are shown in FIG. 15.

Figure 15:
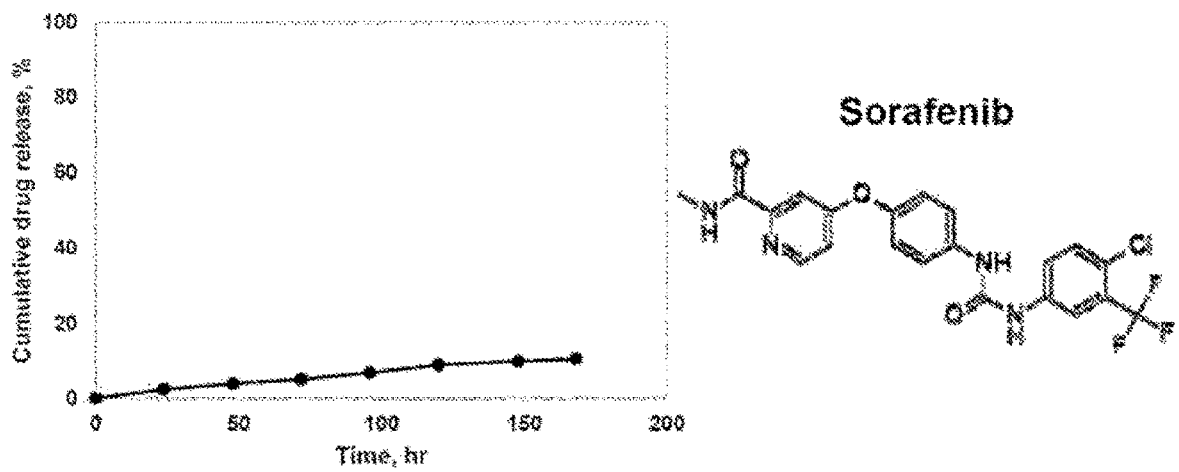

Referring to FIG. 15, it could be seen that sorafenib as the non-soluble bioactive substance was very slowly released due to interaction of sorafenib with the porous silica particles having a hydrophobic substituent.

(4) Retinoic Acid 0.1 mg of retinoic acid-loaded particles was put in PBS (pH 7.4) solution containing 5% ethanol and kept at a temperature of 37° C. while horizontally stirring. The solution containing particles was centrifuged every 24 hours, and an absorbance of the supernatant was measured at a wavelength of 350 nm to determine an amount of released retinoic acid, and results thereof are shown in FIG. 16.

Figure 16:
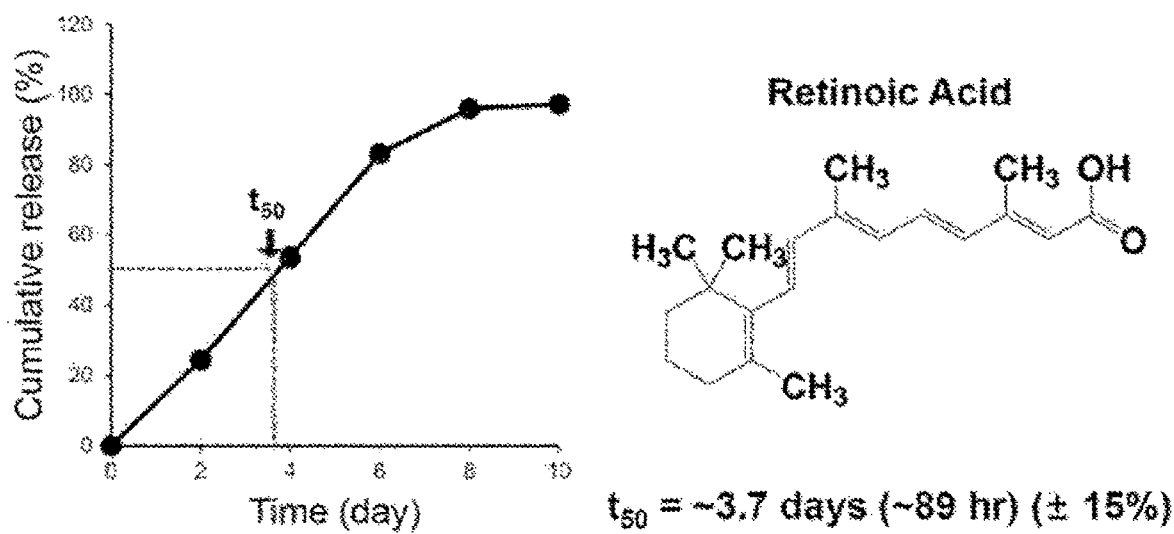

Referring to FIG. 16, it could be seen that the retinoic acid having negative charge was very slowly released due to interaction of the same with the positively charged porous silica particles and almost 100% was released over 10 days.

(5) p53 Peptides 5 mg of particles loaded with p53 peptides was put in 5 mL of 1×PBS containing 10% FBS or 5 mL of 1×PBS, and held in a dynamic environment while rotating at 37° C. and 20 rpm. The solution was centrifuged at 8500 rpm at each time point, and a fluorescent intensity of 5(6)-carboxy fluorescein (FAM) as a fluorescent label coupled to p53 peptide in the supernatant was measured (Absorbance: 480 nm, Emission: 520 nm).

Figure 17:
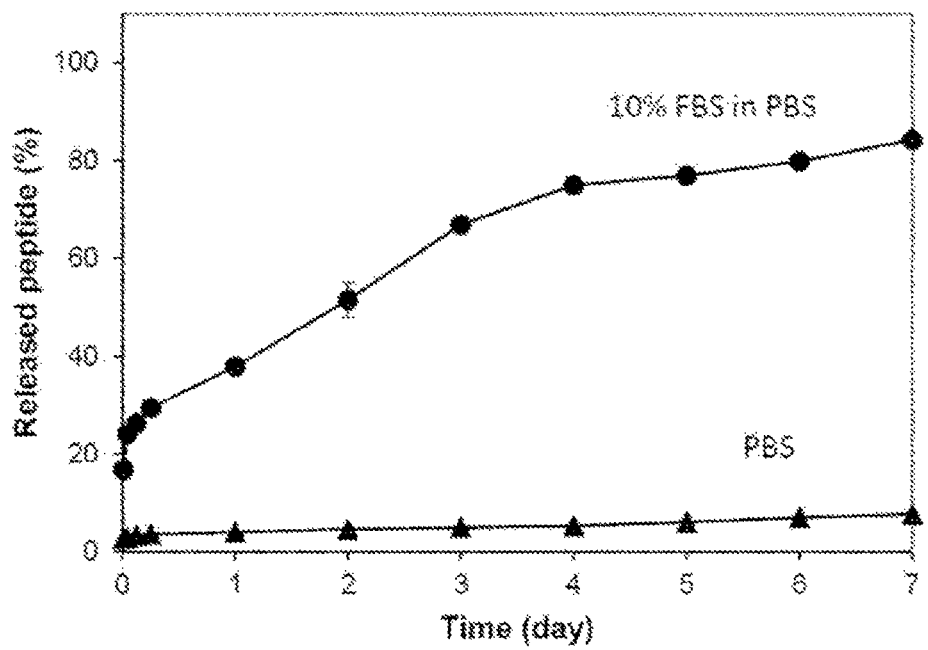

Results thereof are shown in FIG. 17.

Referring to FIG. 17, it could be seen that p53 peptide was loaded in the porous silica particles through a bonding force due to hydrophobic effects, and not released in the PBS solution. However, if a protein such as fetal bovine serum (FBS) is present in the solution, p53 peptide is bond to a hydrophobic segment in FBS protein and can be dissolved in the solution, therefore, this peptide may be released outside the particle. Otherwise, it is presumed that the p53 peptide loaded inside the particle may be released outside the particle and thus the FBS protein will be introduced into the particles.

(6) siRNA

Figure 18:
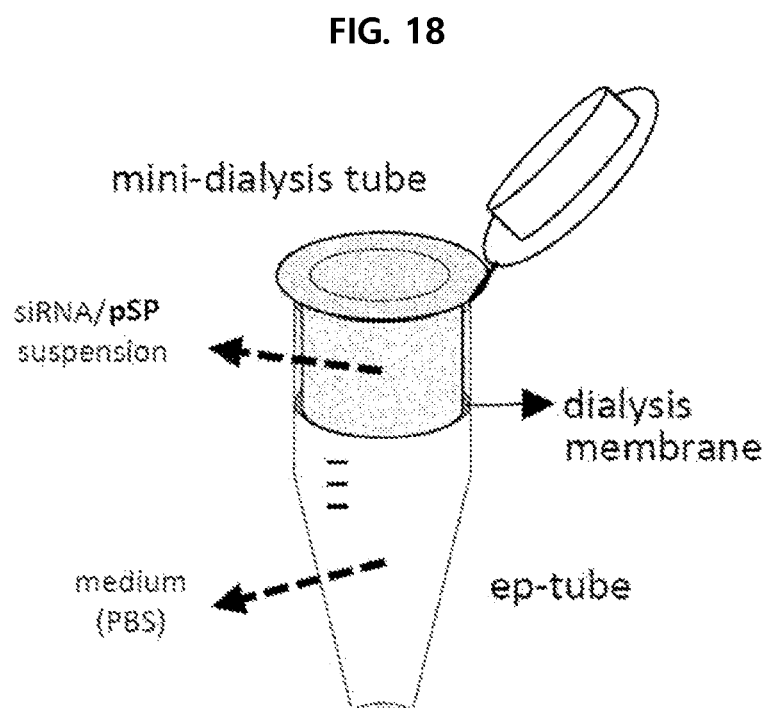
FIG. 18 illustrates a tube used to confirm release of the bioactive substance according to one example

10 µl of the porous silica particles loaded with Cy5-siRNA was re-suspended in SBF (pH 7.4, 37° C.) and then put in a permeable membrane having a pore diameter of 20 kDa (tube in FIG. 18).

Thereafter, the permeable tube was dipped in 1.5 ml of SBF.

Release of siRNA was performed at 37° C. while horizontally stirring at 60 rpm.

Before 24 hours, the released solvent was recovered at a time passing 0.5, 1, 2, 4, 8, 12 and 24 hours. Thereafter, 0.5 ml of released solvent was recovered at an interval of 24 hours for fluorescence measurement, followed by addition of SBF in equal amount.

Figure 19:
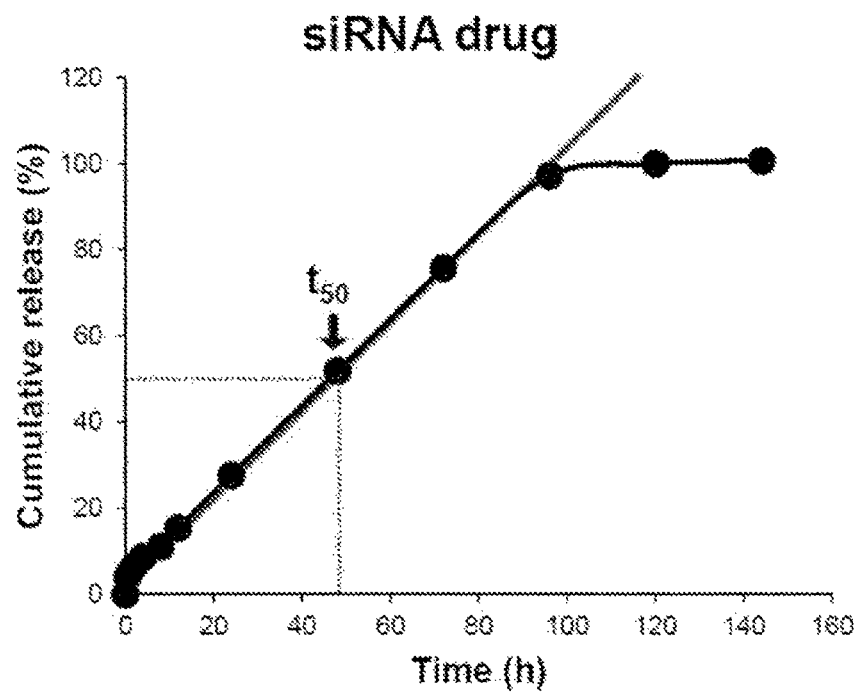
FIGS. 19 to 25 illustrate release profiles over time of bioactive substances, respectively, supported on the porous silica particles according to one embodiment of the present invention.

Fluorescent intensity of Cy5-siRNA was measured at a wavelength of 670 nm (λex=647 nm) to determine a release degree of siRNA, and results thereof are shown in FIG. 19.

Referring to FIG. 19, it could be seen that 50% of siRNA was released over about 48 hours.

(7) Plasmid DNA

The porous silica particles loaded with plasmid DNA (plasmid DNA 1 porous silica particles 50 µg) were re-suspended in PBS (pH 7.4, 37° C.) and then put in a permeable membrane having a pore diameter of 20 kDa (the same tube as the tube in FIG. 18).

Thereafter, the permeable tube was dipped in 1.5 ml of PBS.

Release of plasmid DNA was performed at 37° C. while horizontally stirring at 60 rpm.

Before 24 hours, the released solvent was recovered at a time passing 0.5, 1, 2, 4, 8, 12 and 24 hours. Thereafter, 0.5 ml of released solvent was recovered at an interval of 24 hours for Hoechst-binding assay, followed by addition of PBS in equal amount.

Figure 20:
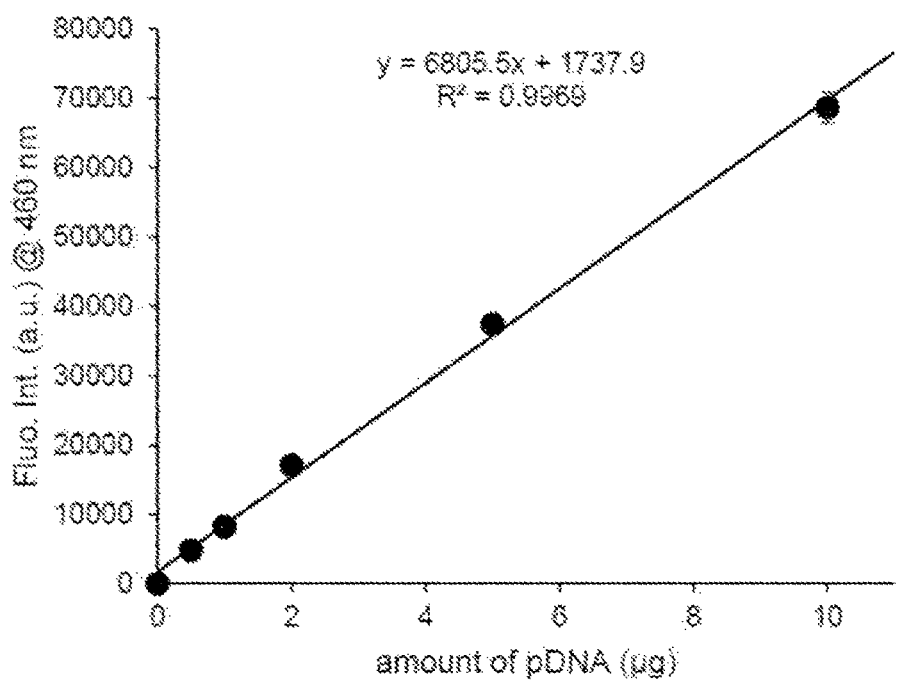
Figure 21:
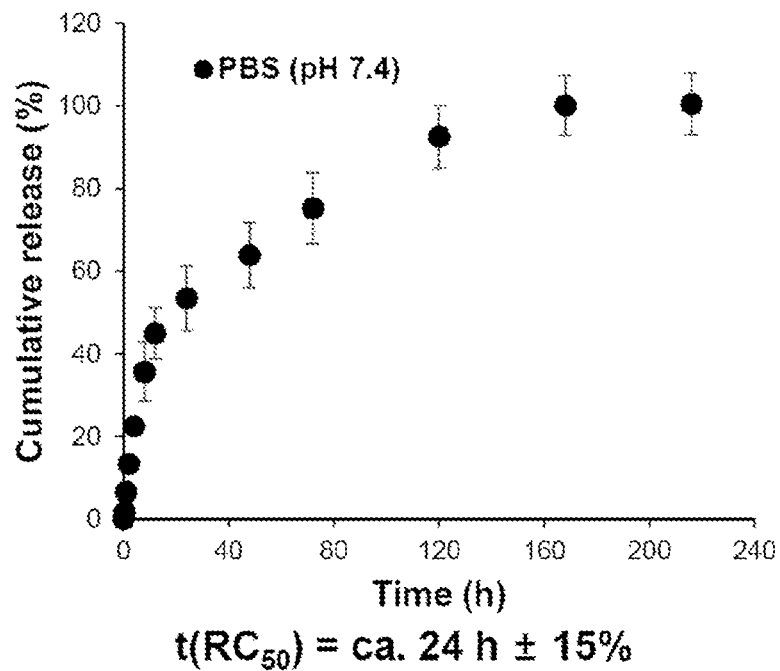

Fluorescent intensity of Hoechst 33342 was measured at a wavelength of 460 nm (λex=360 nm) to determine a release degree of plasmid DNA, and results thereof are shown in FIGS. 20 and 21.

Referring to FIGS. 20 and 21, it could be seen that 50% of plasmid DNA was released over about 24 hours.

(8) Linear DNA

The porous silica particles loaded with linear DNA (linear DNA 3 µg, porous silica particles 100 µg) were re-suspended in PBS (pH 7.4, 37° C.) and then put in a permeable membrane having a pore diameter of 20 kDa (the same tube as the tube in FIG. 18).

Thereafter, the permeable tube was dipped in 1.5 ml of PBS.

Release of linear DNA was performed at 37° C. while horizontally stirring at 60 rpm.

Before 24 hours, the released solvent was recovered at a time passing 0.5, 1, 2, 3, 4, 6, 12 and 24 hours. Thereafter, 0.5 ml of released solvent was recovered at an interval of 24 hours for Hoechst-binding assay, followed by addition of PBS in equal amount.

Figure 22:
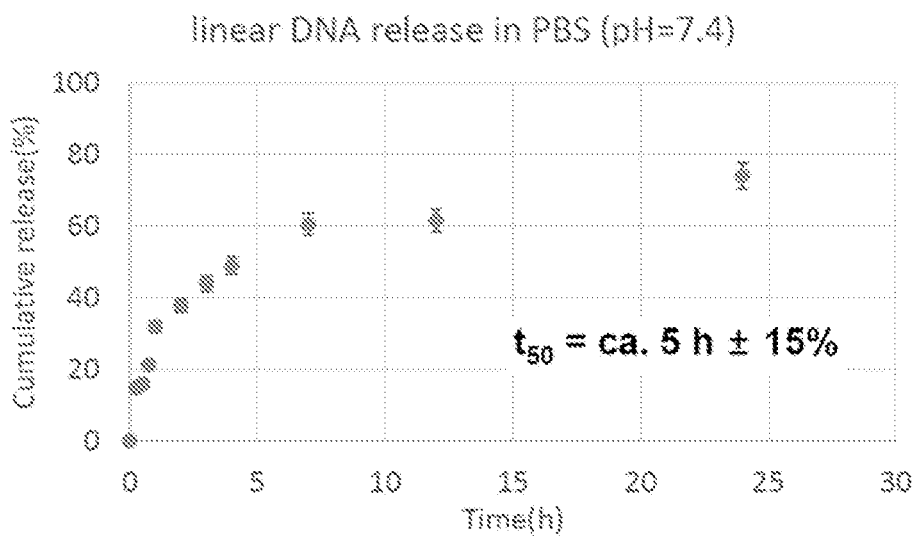

Fluorescent intensity of Hoechst 33342 was measured at a wavelength of 460 nm ($\lambda$ex=360 nm) to determine a release degree of linear DNA, and results thereof are shown in FIG. 22.

Referring to FIG. 22, it could be seen that 50% of linear DNA was released over about 24 hours.

(9) Protein

1) BSA

100 µg of the porous silica particles loaded with BSA having fluorescence labeled therewith was re-suspended in 200 µl of SBF (pH 7.4) or PBS (pH 7.4).

Release of BSA was performed at 37° C. while horizontally stirring at 60 rpm.

At a time point of 6, 12, 24, 48, 96, 144 and 240 hours, 200 µl of released solvent was recovered for fluorescence measurement, followed by addition of SBF or PBS in equal amount.

Figure 23:
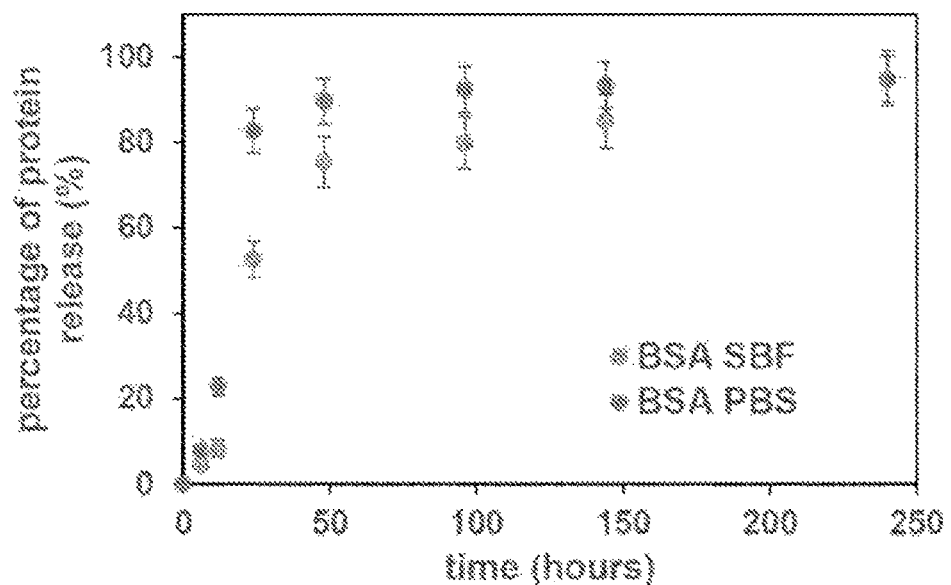

A fluorescent intensity of BSA labeled with fluorescence was measured at a wavelength of 517 nm ($\lambda$ex=492 nm) to determine a release degree of BSA, and results thereof are shown in FIG. 23.

Referring to FIG. 23, it could be seen that BSA may be released in both of SBF and PBS in the sustained manner, and almost 100% is released over 250 hours or more.

2) IgG

100 µg of the porous silica particles loaded with IgG having fluorescence labeled therewith was re-suspended in 200 µl of SBF (pH 7.4) or PBS (pH 7.4).

Release of IgG was performed at 37° C. while horizontally stirring at 60 rpm.

At a time point of 6, 12, 24, 48, 96, 144 and 240 hours, 200 µl of released solvent was recovered for fluorescence measurement, followed by addition of SBF or PBS in equal amount.

Figure 24:
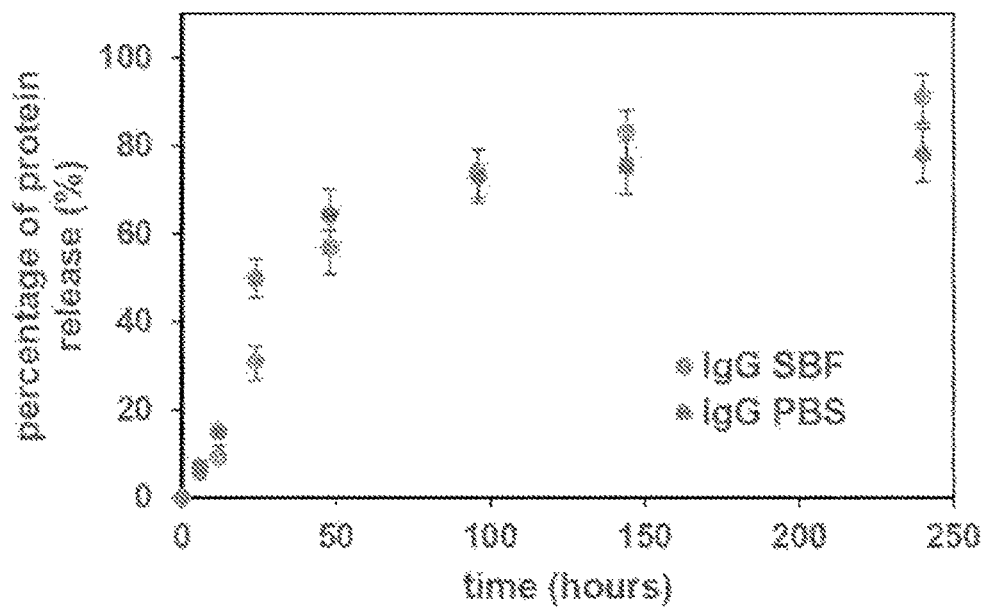

A fluorescent intensity of IgG labeled with fluorescence was measured at a wavelength of 517 nm ($\lambda$ex=492 nm) to determine a release degree of IgG, and results thereof are shown in FIG. 24.

Referring to FIG. 24, it could be seen that IgG may be released in both of SBF and PBS in the sustained manner, and almost 100% is released over 250 hours or more.

3) RNase A

100 µg of the porous silica particles loaded with RNase A having fluorescence labeled therewith was re-suspended in 200 µl of SBF (pH 7.4) or PBS (pH 7.4).

Release of RNase A was performed at 37° C. while horizontally stirring at 60 rpm.

At a time point of 6, 12, 24, 48, 96, 144 and 240 hours, 200 µl of released solvent was recovered for fluorescence measurement, followed by addition of SBF or PBS in equal amount.

Figure 25:
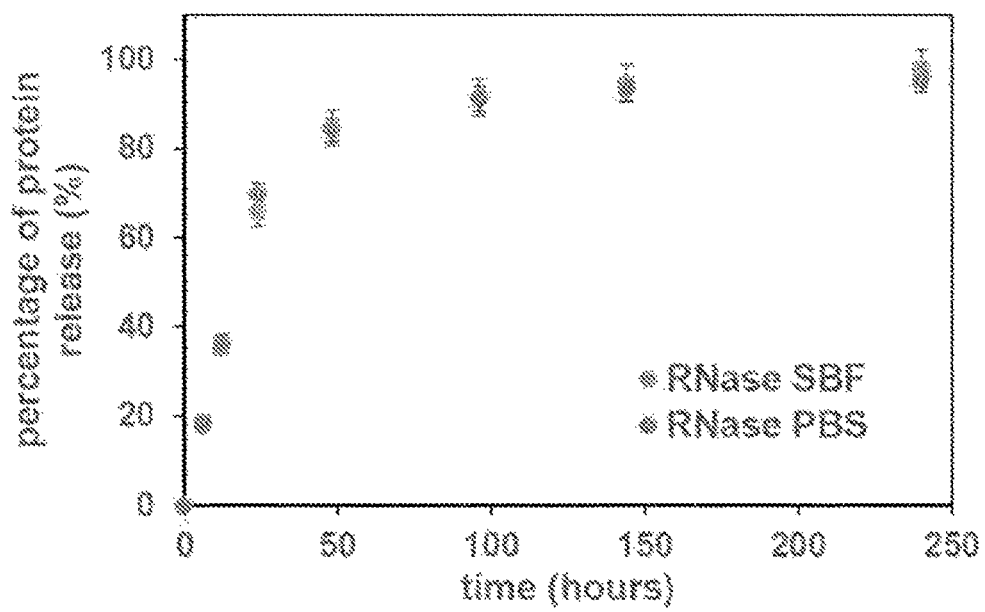

A fluorescent intensity of RNase A labeled with fluorescence was measured at a wavelength of 517 nm ($\lambda$ex=492 nm) to determine a release degree of RNase A, and results thereof are shown in FIG. 25.

Referring to FIG. 25, it could be seen that RNase A may be released in both of SBF and PBS in the sustained manner, and almost 100% is released over 250 hours or more.

4) Cas9

40 µg of the porous silica particles loaded with Cas9 protein/guide RNA complex was suspended in PBS (pH 7.4).

Then, the porous silica particles were treated in a serum free medium on a slide glass with mouse fibroblast cells, that is, 50,000 NIH 3T3 cells flatten thereto, followed by incubation under 5% $CO_2$ and 37° C. conditions.

At time points of 1, 3, 6 and 24 hours, the media were removed, the cells were washed with 1×PBS solution, followed by incubation with 4% paraformaldehyde for 15 minutes to fix the cells.

Then, after washing with PBS, the cells were incubated in a blocking buffer (1×PBS, 5% normal goat serum, 0.3% triton X-100) for 1 hour.

After washing with PBS, the cells were incubated in His tag antibody (Santa Cruz, sc-8036) for 16 hours.

Again, after washing with PBS, the cells were incubated in an anti-mouse secondary antibody (Abcam, ab150113) combined with Alexa Fluor 488 for 2 hours.

After washing with PBS, DAPI (a dye for staining cell nuclei) was treated on the slide glass to stain the cell nuclei. After then, the cells were observed under a fluorescence microscope to detect a distribution of proteins in the cells, and results thereof are shown in FIG. 26.

Figure 26:
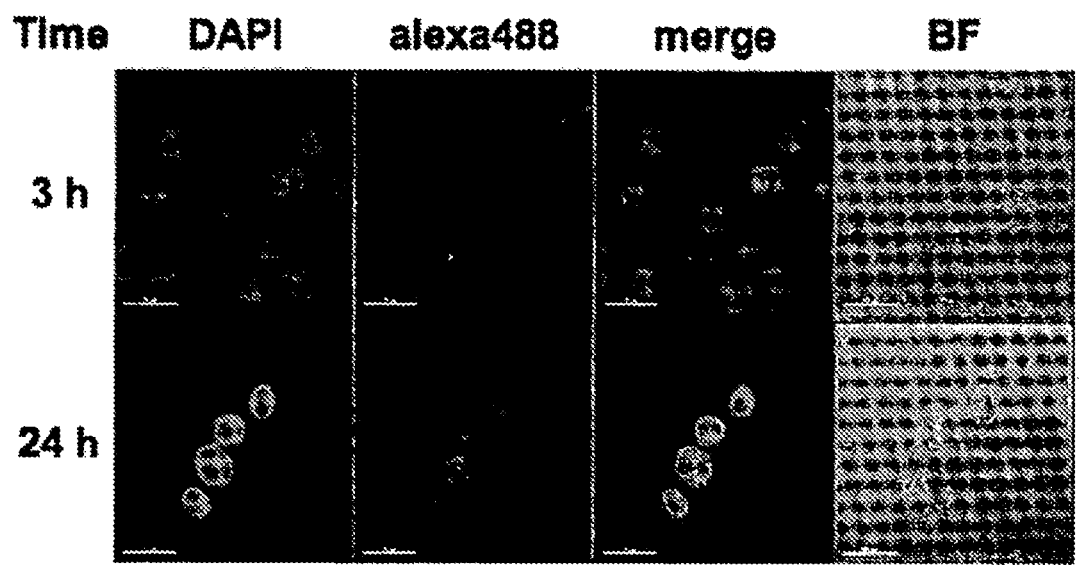
FIG. 26 is microphotographs showing results of supporting Cas9 protein on the porous silica particles according to one embodiment of the present invention, followed by delivering the same into cells.

Referring to FIG. 26, a reagent for staining the cell nuclei, DAPI, is seen as blue in the fluorescence microscopic image to indicate locations of the cell nuclei. Alexa Fluor 488 is a fluorescent dye labeled on Cas9 protein and seen as green in the fluorescence microscopic images to indicate locations of the Cas9 proteins. When the cells are treated with the silica particles loaded with Alexa Fluor 488-labeled Cas9 proteins, followed by DAPI staining, it is possible to detect whether Cas9 protein was introduced into the cells by the silica particles, as well as the locations of the cell nuclei, based on the fluorescence microscopic images.

Referring to the above results, it could be seen that the Cas9 proteins introduced into the cells were mostly observed in a cytoplasm portion after 3 hours from the introduction, and were present inside the cell nuclei after 24 hours. Since the used silica particles are substantially impossible to enter into the cell nucleus, it is understood that Cas9 protein in the cells is released from the silica particles after 24 hours and then is introduced into the nuclei known as organelles wherein Cas9 proteins are accumulated.

6. Delivery of Bioactive Substance

In order to verify that the carrier can serve as a suitable carrier in siRNA delivery studies in an animal level, tumor suppression extent in mice by release of the bioactive substance was measured.

Balb/c nude male mice (5 weeks old) were purchased from Orient Bio Co. Ltd., 3 million of HeLa cells (cervical cancer cells) were dispersed in sterile 1×PBS and subcutaneously injected to mice to grow Xenograft tumors in the mice. When solid tumors in a size of 70 $mm^2$ were found, PBS, FITC-porous silica particles (the porous silica particles in Example 2-(1)-2)(ii)) and FITC-porous silica particles (the porous silica particles in Example 2-(1)-2)(ii)) loaded with Cy5-siRNA, respectively, were administered into the tumors of the mice through injection. Then, fluorescence intensities and a distribution thereof were observed immediately before and after the administration, and after 48 hours from the administration, by means of fluorescence in vivo imaging system (FOBI) (Neo science, Korea).

Figure 27:
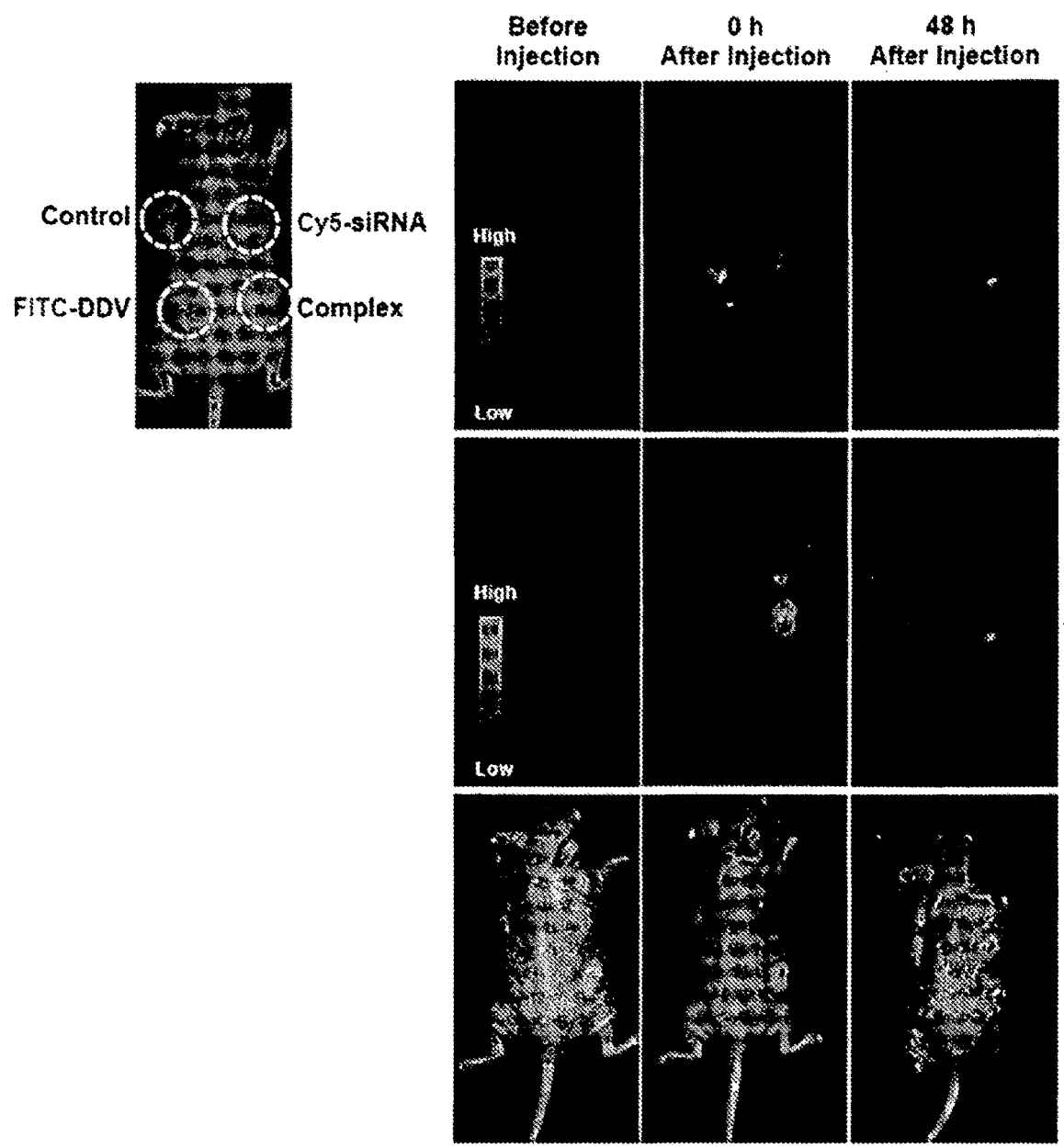
FIG. 27 is microphotographs showing confirmed results of supporting siRNA on the porous silica particles according to one embodiment of the present invention, followed by detecting siRNA release in mice.

FITC labeling was performed by: dispersing 50 mg of silica particles in 1 mL dimethyl sulfoxide (DMSO); adding 25 µg (10 µl) of FITC-NHS (N-hydroxycuccinimide) solution (2.5 mg/mL) to the dispersion; reacting the mixture at room temperature for 18 hours while shielding light with an aluminum foil; purifying the reaction product by centrifugation (8500 rpm, 10 minutes); discarding a supernatant while collecting the settled particles and uniformly dispersing the same in ethanol; and repeatedly purifying the dispersion with ethanol-distilled water, alternately, 3 or 4 times until FITC color is not visible in the supernatant Results thereof are shown in FIG. 27.

Referring to FIG. 27, 'control' denotes PBS administration alone, while 'cy5-siRNA' denotes cy5-siRNA administration alone, 'FITC-DDV' denotes administration of porous silica particles alone, which were indicated as FITC, and 'complex' denotes administration of porous silica particles, which were loaded with cy5-siRNA and labeled with FITC.

Referring to these results, it could be confirmed that siRNA loaded on the particles and delivered into the body may retain activity for a longer period of time and stay longer at an injection site, thereby expressing strong fluorescence even after 48 hours.

A sequence listing electronically submitted with the present application on Aug. 11, 2021 as an ASCII text file named 20210811_Q13519LC21-C_TU_SEQ, created on Aug. 9, 2021 and having a size of 25,000 bytes, is incorporated herein by reference in its entirety.

The invention claimed is:

1. A porous silica particle having a plurality of pores with a diameter of 5 nm to 100 nm, and having 't' of not less than 24 hours, at which a ratio of absorbance measured by Equation 1 below is 1/2:

$$A_t/A_0 \quad \text{[Equation 1]}$$

wherein $A_0$ denotes an absorbance of the porous silica particle measured after putting 5 ml of a suspension including 1 mg/ml of the porous silica particle in a cylindrical permeable membrane having pores with a diameter of 50 kDa;

15 ml of a solvent in contact with the permeable membrane and substantially identical to the suspension is present outside the permeable membrane, inner and outer portions of the permeable membrane are horizontally agitated at 37° C. and 60 rpm, the suspension has pH 7.4; and $A_t$ denotes an absorbance of the porous silica particle measured 't' hour after the measurement of $A_0$.

2. The porous silica particle according to claim 1, wherein the 't' ranges from 24 to 120 hours.

3. The porous silica particle according to claim 1, wherein the porous silica particle is biodegradable.

4. The porous silica particle according to claim 1, wherein the porous silica particle has "t" of 70 to 120 hours, at which a ratio of absorbance measured by Equation 1 is 1/5.

5. The porous silica particle according to claim 1, wherein the pore diameter ranges from 7 nm to 30 nm.

6. The porous silica particle according to claim 1, wherein the porous silica particle has a spherical shape.

7. The porous silica particle according to claim 1, wherein an average diameter of the porous silica particle ranges from 150 nm to 1000 nm.

8. The porous silica particle according to claim 1, wherein the porous silica particle has a BET surface area in a range of 200 $m^2$/g to 700 $m^2$/g.

9. The porous silica particle according to claim 1, wherein a volume of the porous silica particle per gram ranges from 0.7 ml to 2.2 ml.

10. The porous silica particle according to claim 1, wherein the porous silica particle has a hydrophilic substituent or hydrophobic substituent on an outer surface of the particle or inside the pore.

11. The porous silica particle according to claim 1, wherein the porous silica particle is positively or negatively charged on the outer surface of the particle or inside the pore at neutral pH.

* * * * *